US009662204B2

(12) United States Patent
Hariton et al.

(10) Patent No.: US 9,662,204 B2
(45) Date of Patent: May 30, 2017

(54) LOW PROFILE TRANSCATHETER HEART VALVE

(71) Applicant: Edwards Lifesciences Corporation, Irvine, CA (US)

(72) Inventors: Ilia Hariton, Zichron Yaacov (IL); Netanel Benichou, D.N. Hof HaCarmel (IL); Yaacov Nitzan, Kertzeliya (IL); Bella Felsen, Haifa (IL); Diana Nguyen-Thien-Nhon, Irvine, CA (US); Rajesh A. Khanna, Morrisdale (CA); Son V. Nguyen, Irvine, CA (US); Tamir S. Levi, Moshav Ein HaEmek (IL); Itai Pelled, Ramat-Hasharon (IL)

(73) Assignee: Edwards Lifesciences Corporation, Irvine, CA (US)

( * ) Notice: Subject to any disclaimer, the term of this patent is extended or adjusted under 35 U.S.C. 154(b) by 92 days.

(21) Appl. No.: 14/483,862

(22) Filed: Sep. 11, 2014

(65) Prior Publication Data

US 2015/0134052 A1 May 14, 2015

Related U.S. Application Data

(63) Continuation of application No. 13/897,036, filed on May 17, 2013, which is a continuation of application (Continued)

(51) Int. Cl.

*A61F 2/24* (2006.01)
*A61F 2/95* (2013.01)

(52) U.S. Cl.

CPC .......... *A61F 2/2418* (2013.01); *A61F 2/2412* (2013.01); *A61F 2/2433* (2013.01);

(Continued)

(58) Field of Classification Search

CPC .................................. A61F 2/24; A61F 2/224

(Continued)

(56) References Cited

U.S. PATENT DOCUMENTS 3,409,013 A 11/1968 Berry
3,548,417 A 12/1970 Kisher (Continued)

FOREIGN PATENT DOCUMENTS

DE 2246526 A1 3/1973
DE 19532846 A1 3/1997

(Continued)

OTHER PUBLICATIONS

Al-Khaja, et al. "Eleven Years' Experience with Carpentier-Edwards Biological Valves in Relation to Survival and Complications," European Journal of Cardiothoracic Surgery, vol. 1 pp. 305-311. 1989.

(Continued)

*Primary Examiner* — Suzette J Gherbi

(74) *Attorney, Agent, or Firm* — Klarquist Sparkman, LLP; AnneMarie Kaiser

(57) ABSTRACT

An implantable prosthetic valve, according to one embodiment, comprises a frame, a leaflet structure, and a skirt member. The frame can have a plurality of axial struts interconnected by a plurality of circumferential struts. The leaflet structure comprises a plurality of leaflets (e.g., three leaflets arrange to form a tricuspid valve). The leaflet structure has a scalloped lower edge portion secured to the frame. The skirt member can be disposed between the leaflet structure and the frame.

22 Claims, 15 Drawing Sheets

10
14
60
60
82
12
A
18
56
16
56
80
58

Related U.S. Application Data

No. 13/167,549, filed on Jun. 23, 2011, now Pat. No. 8,454,685, which is a continuation of application No. 12/480,603, filed on Jun. 8, 2009, now Pat. No. 7,993,394.

(60) Provisional application No. 61/059,656, filed on Jun. 6, 2008.

(52) U.S. Cl.
CPC .... *A61F 2/2475* (2013.01); *A61F 2002/9522* (2013.01); *A61F 2220/005* (2013.01); *A61F 2220/0033* (2013.01); *A61F 2220/0075* (2013.01); *A61F 2230/0054* (2013.01); *Y10T 29/49863* (2015.01)

(58) Field of Classification Search
USPC ................................................ 623/2.11–2.19
See application file for complete search history.

(56) References Cited

U.S. PATENT DOCUMENTS 3,587,115 A 6/1971 Shiley
3,657,744 A 4/1972 Ersek
3,671,979 A 6/1972 Moulopoulos
3,714,671 A 2/1973 Edwards et al.
3,755,823 A 9/1973 Hancock
4,035,849 A 7/1977 Angell et al.
4,056,854 A 11/1977 Boretos et al.
4,106,129 A 8/1978 Carpentier et al.
4,222,126 A 9/1980 Boretos et al.
4,265,694 A 5/1981 Boretos et al.
4,297,749 A 11/1981 Davis et al.
4,339,831 A 7/1982 Johnson
4,343,048 A 8/1982 Ross et al.
4,345,340 A 8/1982 Rosen
4,373,216 A 2/1983 Klawitter
4,406,022 A 9/1983 Roy
4,441,216 A 4/1984 Ionescu et al.
4,470,157 A 9/1984 Love
4,535,483 A 8/1985 Klawitter et al.
4,574,803 A 3/1986 Storz
4,592,340 A 6/1986 Boyles
4,605,407 A 8/1986 Black et al.
4,612,011 A 9/1986 Kautzky
4,643,732 A 2/1987 Pietsch et al.
4,655,771 A 4/1987 Wallsten
4,692,164 A 9/1987 Dzemeshkevich et al.
4,733,665 A 3/1988 Palmaz
4,759,758 A 7/1988 Gabbay
4,762,128 A 8/1988 Rosenbluth
4,777,951 A 10/1988 Cribier et al.
4,787,899 A 11/1988 Lazarus
4,787,901 A 11/1988 Baykut
4,796,629 A 1/1989 Grayzel
4,820,299 A 4/1989 Philippe et al.
4,829,990 A 5/1989 Thuroff et al.
4,851,001 A 7/1989 Taheri
4,856,516 A 8/1989 Hillstead
4,878,495 A 11/1989 Grayzel
4,878,906 A 11/1989 Lindemann et al.
4,883,458 A 11/1989 Shiber
4,922,905 A 5/1990 Strecker
4,966,604 A 10/1990 Reiss
4,979,939 A 12/1990 Shiber
4,986,830 A 1/1991 Owens et al.
4,994,077 A 2/1991 Dobben
5,007,896 A 4/1991 Shiber
5,026,366 A 6/1991 Leckrone
5,032,128 A 7/1991 Alonso
5,037,434 A 8/1991 Lane
5,047,041 A 9/1991 Samuels
5,059,177 A 10/1991 Towne et al.
5,080,668 A 1/1992 Bolz et al.
5,085,635 A 2/1992 Cragg
5,089,015 A 2/1992 Ross
5,152,771 A 10/1992 Sabbaghian et al.
5,163,953 A 11/1992 Vince
5,167,628 A 12/1992 Boyles
5,192,297 A 3/1993 Hull
5,266,073 A 11/1993 Wall
5,282,847 A 2/1994 Trescony et al.
5,295,958 A 3/1994 Shturman
5,332,402 A 7/1994 Teitelbaum
5,360,444 A 11/1994 Kusuhara
5,370,685 A 12/1994 Stevens
5,397,351 A 3/1995 Pavcnik et al.
5,411,055 A 5/1995 Kane
5,411,552 A 5/1995 Andersen et al.
5,443,446 A 8/1995 Shturman
5,480,424 A 1/1996 Cox
5,500,014 A 3/1996 Quijano et al.
5,545,209 A 8/1996 Roberts et al.
5,545,214 A 8/1996 Stevens
5,549,665 A 8/1996 Vesely et al.
5,554,185 A 9/1996 Block et al.
5,558,644 A 9/1996 Boyd et al.
5,571,175 A 11/1996 Vanney et al.
5,584,803 A 12/1996 Stevens et al.
5,591,185 A 1/1997 Kilmer et al.
5,591,195 A 1/1997 Taheri et al.
5,607,464 A 3/1997 Trescony et al.
5,609,626 A 3/1997 Quijano et al.
5,628,792 A 5/1997 Lentell
5,639,274 A 6/1997 Fischell et al.
5,665,115 A 9/1997 Cragg
5,716,417 A 2/1998 Girard et al.
5,728,068 A 3/1998 Leone et al.
5,749,890 A 5/1998 Shaknovich
5,756,476 A 5/1998 Epstein et al.
5,769,812 A 6/1998 Stevens et al.
5,800,508 A 9/1998 Goicoechea et al.
5,840,081 A 11/1998 Andersen et al.
5,855,597 A 1/1999 Jayaraman
5,855,601 A 1/1999 Bessler et al.
5,855,602 A 1/1999 Angell
5,925,063 A 7/1999 Khosravi
5,957,949 A 9/1999 Leonhardt et al.
6,027,525 A 2/2000 Suh et al.
6,132,473 A 10/2000 Williams et al.
6,168,614 B1 1/2001 Andersen et al.
6,171,335 B1 1/2001 Wheatley et al.
6,174,327 B1 1/2001 Mertens et al.
6,210,408 B1 4/2001 Chandrasekaran et al.
6,217,585 B1 4/2001 Houser et al.
6,221,091 B1 4/2001 Khosravi
6,231,602 B1 5/2001 Carpentier et al.
6,245,102 B1 6/2001 Jayaraman
6,299,637 B1 10/2001 Shaolian
6,302,906 B1 10/2001 Goecoechea et al.
6,350,277 B1 2/2002 Kocur
6,352,547 B1 3/2002 Brown et al.
6,425,916 B1 7/2002 Garrison et al.
6,440,164 B1 8/2002 Di Matteo et al.
6,454,799 B1 9/2002 Schreck
6,458,153 B1 10/2002 Bailey et al.
6,461,382 B1 10/2002 Cao
6,468,660 B2 10/2002 Ogle
6,482,228 B1 11/2002 Norred
6,488,704 B1 12/2002 Connelly et al.
6,527,979 B2 3/2003 Constantz
6,569,196 B1 5/2003 Vesely et al.
6,582,462 B1 6/2003 Andersen et al.
6,605,112 B1 8/2003 Moll
6,652,578 B2 11/2003 Bailey et al.
6,689,123 B2 2/2004 Pinchasik
6,716,244 B2 4/2004 Klaco
6,730,118 B2 5/2004 Spenser et al.
6,733,525 B2 5/2004 Yang et al.
6,767,362 B2 7/2004 Schreck
6,769,161 B2 8/2004 Brown et al.
6,783,542 B2 8/2004 Eidenschink
6,830,584 B1 12/2004 Seguin

(56) References Cited

U.S. PATENT DOCUMENTS 6,878,162 B2 4/2005 Bales et al.
6,893,460 B2* 5/2005 Spenser ................ A61F 2/2412 623/2.14
6,908,481 B2 6/2005 Cribier
6,936,067 B2 8/2005 Buchanan
7,018,406 B2 3/2006 Seguin et al.
7,018,408 B2 3/2006 Bailey et al.
7,096,554 B2 8/2006 Austin et al.
7,225,518 B2 6/2007 Eidenschink et al.
7,276,078 B2 10/2007 Spenser et al.
7,276,084 B2 10/2007 Yang et al.
7,318,278 B2 1/2008 Zhang et al.
7,374,571 B2 5/2008 Pease et al.
7,393,360 B2 7/2008 Spenser et al.
7,462,191 B2 12/2008 Spenser et al.
7,510,575 B2 3/2009 Spenser et al.
7,563,280 B2 7/2009 Anderson et al.
7,585,321 B2 9/2009 Cribier
7,618,446 B2 11/2009 Andersen et al.
7,618,447 B2 11/2009 Case et al.
7,655,034 B2 2/2010 Mitchell et al.
7,785,366 B2 8/2010 Maurer et al.
7,959,672 B2 6/2011 Salahieh et al.
7,993,394 B2 8/2011 Hariton et al.
8,029,556 B2 10/2011 Rowe
8,167,932 B2 5/2012 Bourang
8,291,570 B2* 10/2012 Eidenschink ............ A61F 2/95 29/283.5
8,449,606 B2 5/2013 Eliasen et al.
8,454,685 B2* 6/2013 Hariton ................ A61F 2/2412 623/2.17
8,747,463 B2 6/2014 Fogarty et al.
9,078,781 B2 7/2015 Ryan et al.
2001/0021872 A1 9/2001 Bailey et al.
2002/0026094 A1 2/2002 Roth
2002/0032481 A1 3/2002 Gabbay
2002/0138135 A1 9/2002 Duerig et al.
2002/0173842 A1 11/2002 Buchanan
2003/0050694 A1 3/2003 Yang et al.
2003/0100939 A1 5/2003 Yodfat et al.
2003/0158597 A1 8/2003 Quiachon et al.
2003/0212454 A1 11/2003 Scott et al.
2004/0039436 A1 2/2004 Spenser et al.
2004/0186563 A1 9/2004 Lobbi
2004/0186565 A1 9/2004 Schreck
2004/0260389 A1 12/2004 Case et al.
2005/0096736 A1 5/2005 Osse et al.
2005/0203614 A1 9/2005 Forster et al.
2005/0203617 A1 9/2005 Forster et al.
2005/0234546 A1 10/2005 Nugent et al.
2006/0004469 A1* 1/2006 Sokel ................... A61F 2/2415 29/516
2006/0025857 A1 2/2006 Bergheim et al.
2006/0058872 A1 3/2006 Salahieh et al.
2006/0149350 A1 7/2006 Patel et al.
2006/0229719 A1 10/2006 Marquez et al.
2006/0259137 A1 11/2006 Artof et al.
2007/0005131 A1 1/2007 Taylor
2007/0010877 A1 1/2007 Salahieh et al.
2007/0112422 A1 5/2007 Dehdashtian
2007/0203503 A1 8/2007 Salahieh et al.
2007/0203575 A1 8/2007 Forster et al.
2007/0203576 A1 8/2007 Lee et al.
2007/0233228 A1 10/2007 Eberhardt et al.
2007/0260305 A1 11/2007 Drews et al.
2007/0265700 A1 11/2007 Eliasen et al.
2008/0114442 A1 5/2008 Mitchell et al.
2008/0125853 A1 5/2008 Bailey et al.
2008/0154355 A1 6/2008 Benichou et al.
2008/0183271 A1 7/2008 Frawley et al.
2008/0275537 A1 11/2008 Limon
2009/0125118 A1* 5/2009 Gong ................... A61F 2/0077 623/23.7
2009/0157175 A1 6/2009 Benichou
2009/0276040 A1 11/2009 Rowe et al.
2009/0281619 A1* 11/2009 Le ........................ A61M 25/01 623/2.11
2009/0299452 A1* 12/2009 Eidenschink ............ A61F 2/95 623/1.11
2009/0319037 A1 12/2009 Rowe et al.
2010/0049313 A1 2/2010 Alon et al.
2010/0198347 A1 8/2010 Zakay et al.
2010/0204781 A1 8/2010 Alkhatib
2011/0015729 A1 1/2011 Jimenez et al.
2011/0319991 A1* 12/2011 Hariton ................ A61F 2/2412 623/2.14
2012/0123529 A1 5/2012 Levi et al.
2013/0023985 A1 1/2013 Khairkhahan et al.
2013/0310926 A1* 11/2013 Hariton ................ A61F 2/2412 623/2.11
2013/0317598 A1 11/2013 Rowe et al.
2014/0209238 A1* 7/2014 Bonyuet ............... A61F 2/2415 156/294

FOREIGN PATENT DOCUMENTS

DE 19546692 A1 6/1997
DE 19857887 A1 7/2000
DE 19907646 A1 8/2000
DE 10049812 A1 4/2002
DE 10049813 C1 4/2002
DE 10049814 A1 4/2002
DE 10049815 A1 4/2002
EP 0103546 A1 3/1984
EP 0144167 A2 6/1985
EP 0592410 A1 4/1994
EP 0597967 A1 5/1994
EP 0850607 A1 7/1998
EP 1057460 A1 12/2000
EP 1088529 A2 4/2001
EP 1570809 A1 9/2005
EP 1796597 A2 6/2007
FR 2788217 A1 7/2000
FR 2815844 A1 5/2002
GB 2056023 A 3/1981
SU 1271508 A1 11/1986
WO 91/17720 A1 11/1991
WO 92/17118 A1 10/1992
WO 93/01768 A1 2/1993
WO 97/24080 A1 7/1997
WO 98/29057 A1 7/1998
WO 9930646 A1 6/1999
WO 99/33414 A1 7/1999
WO 99/40964 A1 8/1999
WO 99/47075 A1 9/1999
WO 00/18333 A1 4/2000
WO 00/41652 A1 7/2000
WO 00/47139 A1 8/2000
WO 01/49213 A2 1/2001
WO 01/35878 A2 5/2001
WO 01/62189 A1 8/2001
WO 0154624 A1 8/2001
WO 0154625 A1 8/2001
WO 01/64137 A1 9/2001
WO 01/76510 A2 10/2001
WO 02/22054 A1 3/2002
WO 02/36048 A1 5/2002
WO 02/41789 A2 5/2002
WO 02/43620 A1 6/2002
WO 02/47575 A2 6/2002
WO 02/49540 A2 6/2002
WO 03/047468 A1 6/2003
WO 2005034812 A1 4/2005
WO 2005084595 A1 9/2005
WO 2005102015 A2 11/2005
WO 2006/014233 A2 2/2006
WO 2006/034008 A2 3/2006
WO 2006111391 A1 10/2006
WO 2006/138173 A2 12/2006
WO 2007047488 A2 4/2007
WO 200767942 A1 6/2007
WO 2007097983 A2 8/2007

(56) References Cited

FOREIGN PATENT DOCUMENTS

| | | | |
|---|---|---|---|
| WO | 2008/005405 | A2 | 1/2008 |
| WO | 2008/035337 | A2 | 3/2008 |
| WO | 2008091515 | A2 | 7/2008 |
| WO | 2008/147964 | A1 | 12/2008 |
| WO | 2008/150529 | A1 | 12/2008 |
| WO | 2009033469 | A1 | 3/2009 |
| WO | 2010121076 | A2 | 10/2010 |

OTHER PUBLICATIONS

Andersen, et al., Transluminal implantation of artificial heart valves. Description of a new expandable aortic valve and Initial results withimplantation by catheter technique in closed chest pigs. European Heart Journal (1992), 13, 704-708. cited by other.

Andersen, Henning Rud, History of Percutaneous Aortic Valve Prosthesis, Herz 34 2009 Nr. 5, Urban & Vogel, pp. 343-346, Skejby University Hospital Department of Cardiology, Aarhus, Denmark. cited by other.

Bailey, S. "Percutaneous Expandable Prosthetic Valves," Textbook of Interventional Cardiology vol. 2, 2nd Ed. pp. 1268-1276. 1994.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Ross, "Aortic Valve Surgery," At a meeting of the Council on 4th Aug. 1966. pp. 192-197.

Sabbah, et al. "Mechanical Factors in the Degeneration of Porcine Bioprosthetic Valves: an Overview," Journal of cardiac Surgery, vol. 4, No. 4. pp. 302-309. 1989.

Uchida, "Modifications of Gianturco Expandable Wire Stents," American Journal of Roentgenology, vol. 150. pp. 1185-1187. 1986.

Wheatley, "Valve Prostheses," Operative Surgery, 4th ed. pp. 415-424. 1986.

* cited by examiner 14
10
12
16

84
60
14
18
56
56
16

58
14
16
59
68

18
30
18
12
24
26
24
78
32
32
18
30
22
22
30
26
60
20
20

90
40
18

26
26
12
24
24
36c
18
28
28
22
T
36b
30
30
26
20
26
26
36a
T
34
34
34
26
26
26

48
40
52d
46
18
52c
18
54
54
44
52b
26
26
42
52a
50
26
50
50
50

76
62
76
76
76

LOW PROFILE TRANSCATHETER HEART VALVE

CROSS REFERENCE TO RELATED APPLICATIONS

This application is a continuation of U.S. patent application Ser. No. 13/897,036, filed May 17, 2013, which is a continuation of U.S. patent application Ser. No. 13/167,549, filed Jun. 23, 2011, which is a continuation of U.S. patent application Ser. No. 12/480,603, filed Jun. 8, 2009, which claims the benefit of U.S. Patent Application No. 61/059,656, filed Jun. 6, 2008, the entire disclosures which are incorporated herein by reference.

FIELD

The present disclosure relates to implantable devices and, more particularly, to valve prosthetics for implantation into body ducts, such as native heart valve annuluses.

DESCRIPTION OF THE RELATED ART

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans.

Various surgical techniques may be used to repair a diseased or damaged valve. In a valve replacement operation, the damaged leaflets are excised and the annulus sculpted to receive a replacement valve. Due to aortic stenosis and other heart valve diseases, thousands of patients undergo surgery each year wherein the defective native heart valve is replaced by a prosthetic valve, either bioprosthetic or mechanical. Another less drastic method for treating defective valves is through repair or reconstruction, which is typically used on minimally calcified valves. The problem with surgical therapy is the significant insult it imposes on these chronically ill patients with high morbidity and mortality rates associated with surgical repair.

When the valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective valves are deemed inoperable because their condition is too frail to withstand the procedure. By some estimates, more than 50% of the subjects suffering from aortic stenosis who are older than 80 years cannot be operated on for aortic valve replacement.

Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For instance, U.S. Pat. Nos. 5,411,522 and 6,730,118, which are incorporated herein by reference, describe collapsible transcatheter heart valves that can be percutaneously introduced in a compressed state on a catheter and expanded in the desired position by balloon inflation or by utilization of a self-expanding frame or stent.

An important design parameter of a transcatheter heart valve is the diameter of the folded or crimped profile. The diameter of the crimped profile is important because it directly influences the physician's ability to advance the valve through the femoral artery or vein. More particularly, a smaller profile allows for treatment of a wider population of patients, with enhanced safety.

SUMMARY

The present disclosure is directed toward new and non-obvious methods and apparatuses relating to prosthetic valves, such as heart valves.

In one representative embodiment, an implantable prosthetic valve comprises a radially collapsible and expandable frame, or stent, and a leaflet structure comprising a plurality of leaflets. The leaflet structure has a scalloped lower edge portion that is positioned inside of and secured to the frame. The valve can further include an annular skirt member, which can be disposed between the frame and the leaflet structure such that the scalloped lower edge portion can be attached to an inner surface of the skirt member. Each leaflet can have an upper edge, a curved lower edge and two side flaps extending between respective ends of the upper edge and the lower edge, wherein each side flap is secured to an adjacent side flap of another leaflet to form commissures of the leaflet structure. Each commissure can be attached to one of the commissure attachment posts, and a reinforcing bar can be positioned against each side flap for reinforcing the attachments between the commissures and the commissure attachment posts.

The frame can comprise a plurality of angularly spaced, axial struts that are interconnected by a plurality of rows of circumferential struts. Each row of circumferential struts desirably includes struts arranged in a zig-zag or saw-tooth pattern extending around the circumference of the frame.

In certain embodiments, at least one row, and preferably all rows, of circumferential struts include pairs of circumferential struts extending between two axial struts. Each strut of the pair has one end connected to a respective axial strut and another end interconnected to an adjacent end of the other strut of the same pair by a crown portion such that a gap exists between the adjacent ends of the struts. The angle between the struts of each pair desirably is between about 90 and 110 degrees, with about 100 degrees being a specific example. The frame desirably is made of a nickel-cobalt based alloy, such as a nickel cobalt chromium molybdenum alloy (e.g., MP35N™).

In another representative embodiment, an implantable prosthetic valve comprises a radially collapsible and expandable annular frame and a leaflet structure supported by the frame. The frame can comprise a plurality of interconnected struts defining a plurality of open cells in the frame. The valve further includes an annular cover member disposed on and covering the cells of at least a portion of the frame. The cover member desirably comprises an elastomer, such as silicon, that can expand and stretch when the valve is expanded from a crimped state to an expanded state.

The cover member may be a thin sleeve of silicon that surrounds at least a portion of the frame. Alternatively, the cover member may be formed by dipping at least a portion of the frame in silicon or another suitable elastomer in liquefied form.

In another representative embodiment, a method is disclosed for crimping an implantable prosthetic valve having a frame and leaflets supported by the frame. The method comprises placing the valve in the crimping aperture of a crimping device such that a compressible material is disposed between the crimping jaws of the crimping device and the frame of the valve. Pressure is applied against the compressible material and the valve with the crimping jaws to radially crimp the valve to a smaller profile and compress the compressible material against the valve such that the compressible material extends into open cells of the frame and pushes the leaflets away from the inside of the frame.

The foregoing and other features and advantages of the invention will become more apparent from the following detailed description, which proceeds with reference to the accompanying figures.

DETAILED DESCRIPTION

Figure 1:
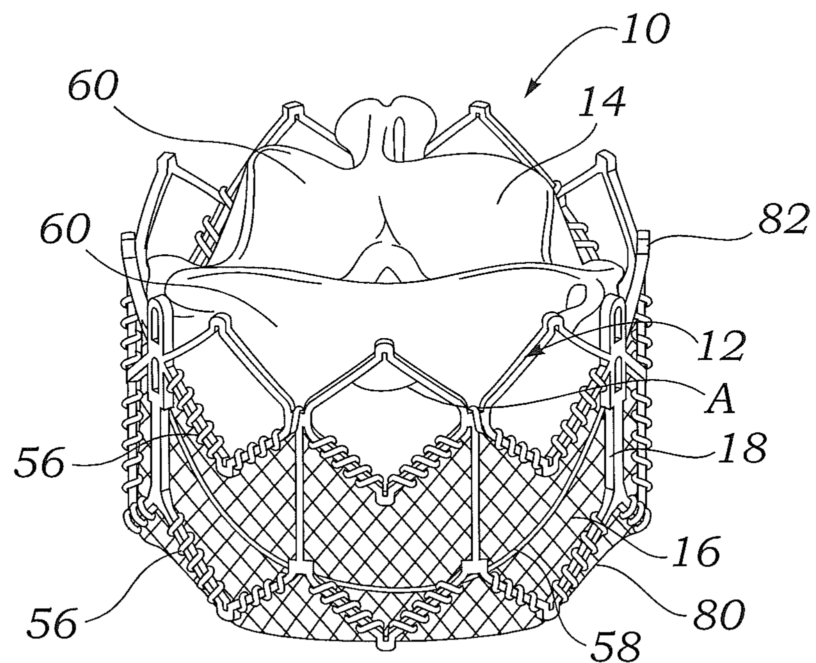
FIG. 1 is a perspective view of a representative embodiment of a prosthetic heart valve.
Figure 2:
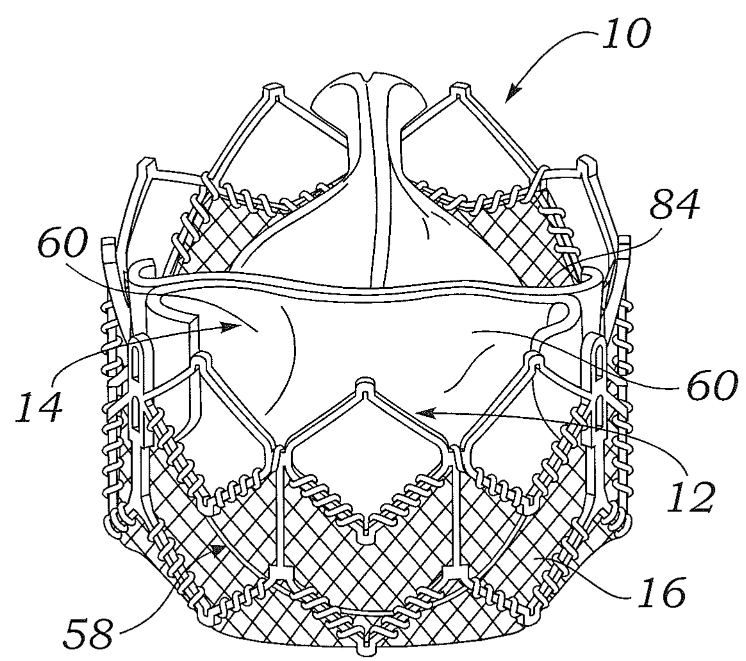
FIG. 2 is another perspective view of the prosthetic valve of FIG. 1.
Figure 3:
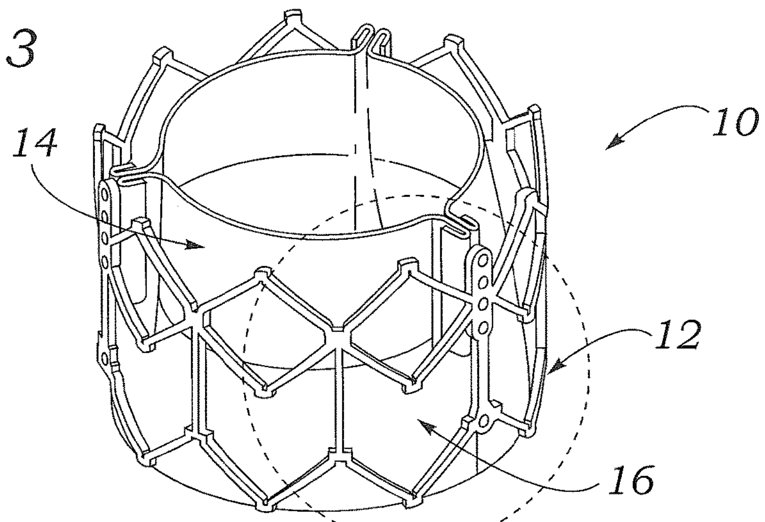
FIG. 3 is another perspective view of the prosthetic valve of FIG. 1.
Figure 4:
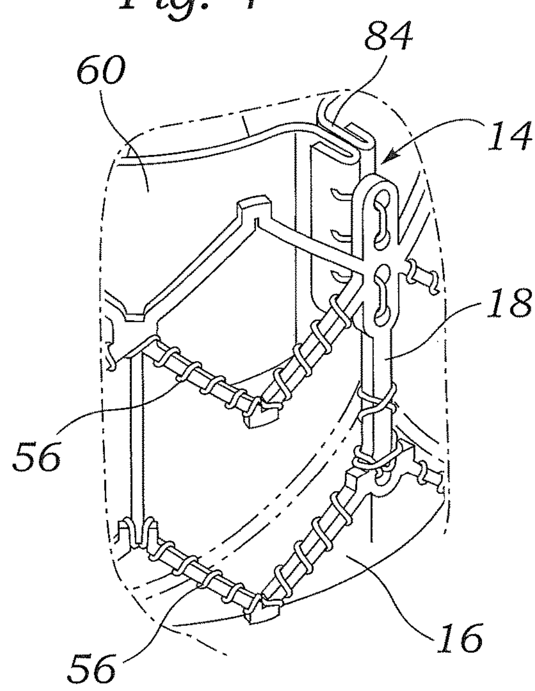
FIG. 4 is an enlarged view of a section of the valve shown in FIG. 3.

FIGS. 1 and 2 illustrate an implantable prosthetic valve 10, according to one embodiment. Valve 10 in the illustrated embodiment generally comprises a frame, or stent, 12, a leaflet structure 14 supported by the frame, and a skirt 16 secured to the outer surface of the leaflet structure. Valve 10 typically is implanted in the annulus of the native aortic valve but also can be adapted to be implanted in other native valves of the heart or in various other ducts or orifices of the body. Valve 10 has a “lower” end 80 and an “upper” end 82. In the context of the present application, the terms “lower” and “upper” are used interchangeably with the terms “inflow” and “outflow”, respectively. Thus, for example, the lower end 80 of the valve is its inflow end and the upper end 82 of the valve is its outflow end.

Valve 10 and frame 12 are configured to be radially collapsible to a collapsed or crimped state for introduction into the body on a delivery catheter and radially expandable to an expanded state for implanting the valve at a desired location in the body (e.g., the native aortic valve). Frame 12 can be made of a plastically-expandable material that permits crimping of the valve to a smaller profile for delivery and expansion of the valve using an expansion device such as the balloon of a balloon catheter. Exemplary plastically-expandable materials that can be used to form the frame are described below. Alternatively, valve 10 can be a so-called self-expanding valve wherein the frame is made of a self-expanding material such as Nitinol. A self-expanding valve can be crimped to a smaller profile and held in the crimped state with a restraining device such as a sheath covering the valve. When the valve is positioned at or near the target site, the restraining device is removed to allow the valve to self-expand to its expanded, functional size.

Figure 5:
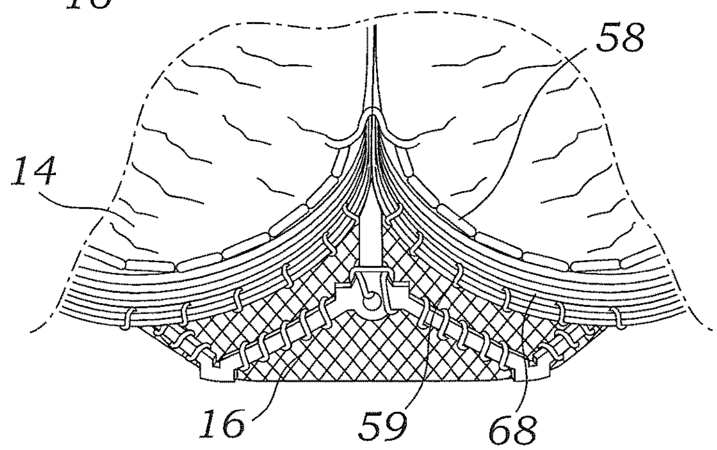
FIG. 5 is a bottom perspective view of the prosthetic valve of FIG. 1 showing the inside of the valve.
Figure 7:
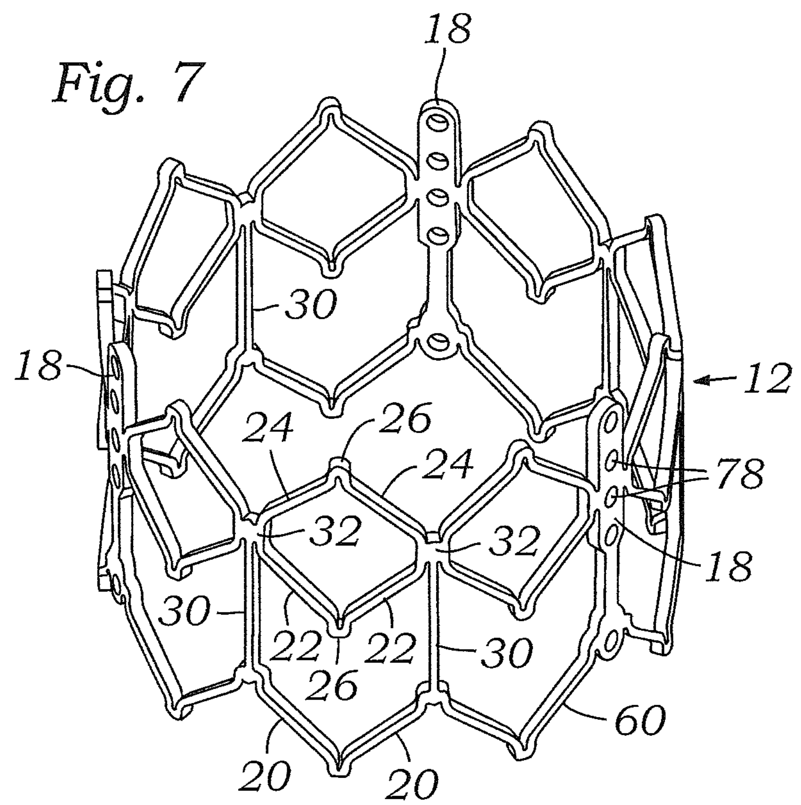
FIG. 7 is a perspective view of the frame of the prosthetic valve of FIG. 1.

Referring also to FIG. 7 (which shows the frame alone for purposes of illustration), frame 12 is an annular, stent-like structure having a plurality of angularly spaced, vertically extending, commissure attachment posts, or struts, 18. Posts 18 can be interconnected via a lower row 36*a* of circumferentially extending struts 20 and first and second rows upper rows 36*b*, 36*c*, respectively, of circumferentially extending struts 22 and 24, respectively. The struts in each row desirably are arranged in a zig-zag or generally saw-tooth like pattern extending in the direction of the circumference of the frame as shown. Adjacent struts in the same row can be interconnected to one another as shown in FIGS. 1 and 5 to form an angle A, which desirably is between about 90 and 110 degrees, with about 100 degrees being a specific example. The selection of angle A between approximately 90 and 110 degrees optimizes the radial strength of frame 12 when expanded yet still permits the frame 12 to be evenly crimped and then expanded in the manner described below.

In the illustrated embodiment, pairs of adjacent circumferential struts in the same row are connected to each other by a respective, generally U-shaped crown structure, or crown portion, 26. Crown structures 26 each include a horizontal portion extending between and connecting the adjacent ends of the struts such that a gap 28 is defined between the adjacent ends and the crown structure connects the adjacent ends at a location offset from the strut's natural point of intersection. Crown structures 26 significantly reduce residual strains on the frame 12 at the location of struts 20, 22, 24 during crimping and expanding of the frame 20 in the manner described below. Each pair of struts 22 connected at a common crown structure 26 forms a cell with an adjacent pair of struts 24 in the row above. Each cell can be connected to an adjacent cell at a node 32. Each node 32 can be interconnected with the lower row of struts by a respective vertical (axial) strut 30 that is connected to and extends between a respective node 32 and a location on the lower row of struts 20 where two struts are connected at their ends opposite crown structures 26.

In certain embodiments, lower struts 20 have a greater thickness or diameter than upper struts 22, 24. In one implementation, for example, lower struts 20 have a thickness T (FIG. 9) of about 0.42 mm and upper struts 22, 24 have a thickness T of about 0.38 mm Because there is only one row of lower struts 20 and two rows of upper struts 22, 24 in the illustrated configuration, enlargement of lower struts 20 with respect to upper struts 22, 24 enhances the radial strength of the frame at the lower area of the frame and allows for more uniform expansion of the frame.

Figure 9:
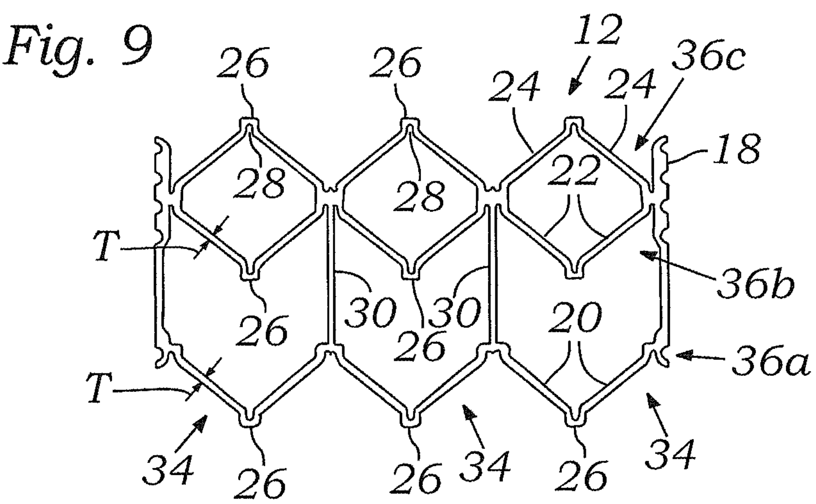
FIG. 9 is a flattened view of 120-degree segment of the frame shown in FIG. 7.

FIG. 9 shows a flattened view of a 120-degree segment of frame 12 shown in FIG. 7, the segment comprising a portion of the frame extending between two posts 18. As shown, the frame segment has three columns 34 and three rows 36*a*, 36*b*, 36*c* of struts per segment. Each column 34 is defined by the adjoining pairs of struts 20, 22, 24 extending between two axially extending struts 18, 30. Frame 12 desirably is comprised of three 120-degree segments, with each segment being bounded by two posts 18. Accordingly, frame 12 in the illustrated embodiment includes 9 total columns per frame.

The number of columns and rows desirably is minimized to reduce the overall crimp profile of the valve, as further discussed below. The arrangement of FIGS. 7 and 9 typically is used for valves that are less than about 29 mm in diameter, and are most suitable for valves that are about 20-26 mm in diameter. In working examples of valves comprising frame 12, a 20-mm valve can be crimped to a diameter of about 17 Fr, a 23-mm valve can be crimped to a diameter of about 18 Fr and a 26-mm valve can be crimped to a diameter of about 19 Fr. For valves that are about 29 mm and larger in diameter, it may be desirable to add another row and column of struts.

Figure 8:
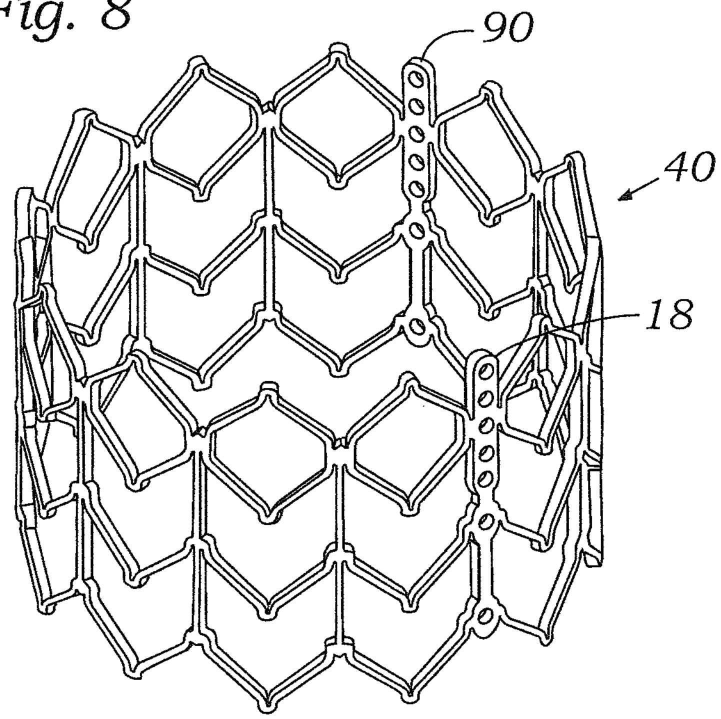
FIG. 8 is a perspective view of an alternative embodiment of a frame that can be used in the prosthetic valve of FIG. 1.
Figure 10:
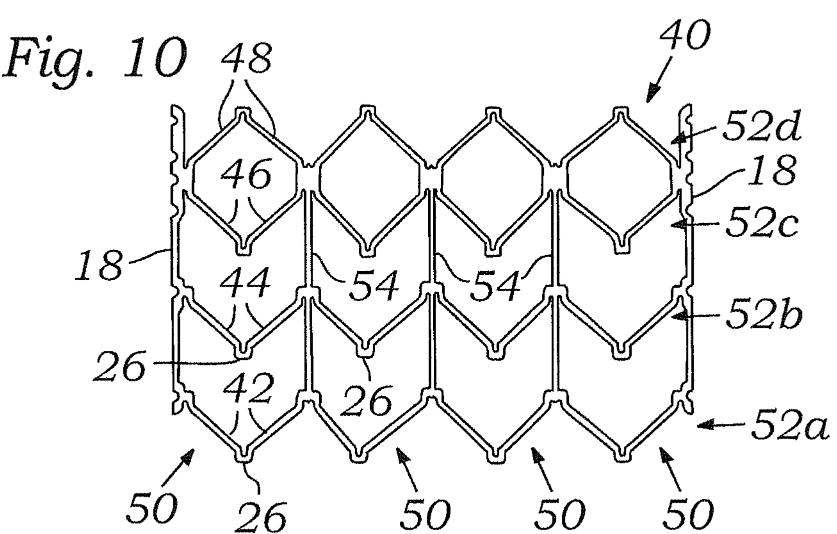
FIG. 10 is a flattened view of 120-degree segment of the frame shown in FIG. 8.

For example, FIGS. 8 and 10 show an alternative frame 40 that is similar to frame 12 except that frame 40 has four rows of struts (a lowermost, first row 52*a* of struts 42, a second row 52*b* of struts 44, a third row 52*c* of struts 46, and an uppermost row 52*d* of struts 48) instead of three rows of struts, as well as four columns 50 of struts for each 120-degree frame segment instead of three columns of struts. FIG. 10 shows a flattened view of a 120-degree segment of frame 40 shown in FIG. 8. Frame 40 in the illustrated embodiment includes three such 120-degree segments, providing 12 total columns 50 of struts for the frame.

Struts 46 of the third row desirably are facing in the opposite direction of the struts 48 of the fourth row (i.e., the apexes or crown portions are facing in the opposite direction), to help avoid buckling of the vertical posts of the frame during crimping and expansion of the valve. Struts 44 of the second row can be arranged so as to be facing in the same direction as the struts 42 of the first row as shown (i.e., the apexes or crown portions are facing in the same direction). Alternatively, struts 44 of the second row can be facing in the opposing direction from struts 42 of the first row so as to form square cells, like the cells formed by the struts 46, 48 of the third and fourth rows, respectively. Frame 40 can also include axially extending struts 54 connected to and extending between the ends of each strut 42, 44, 46, and 48 aligned in a column 50 that are not connected to a post 18. As noted above, frame 40 is most suitable for valves 29 mm and larger in diameter (when expanded to its functional size). In a working example of a valve incorporating frame 40, a 29-mm valve can be crimped to a diameter of about 21 Fr.

Suitable plastically-expandable materials that can be used to form the frame include, without limitation, stainless steel, a nickel based alloy (e.g., a nickel-cobalt-chromium alloy), polymers, or combinations thereof. In particular embodiments, frame 20 is made of a nickel-cobalt-chromium-molybdenum alloy, such as MP35N™ (tradename of SPS Technologies), which is equivalent to UNS R30035 (covered by ASTM F562-02). MP35N™/UNS R30035 comprises 35% nickel, 35% cobalt, 20% chromium, and 10% molybdenum, by weight. It has been found that the use of MP35N to form frame 20 provides superior structural results over stainless steel. In particular, when MP35N is used as the frame material, less material is needed to achieve the same or better performance in radial and crush force resistance, fatigue resistances, and corrosion resistance. Moreover, since less material is required, the crimped profile of the frame can be reduced, thereby providing a lower profile valve assembly for percutaneous delivery to the treatment location in the body.

Referring again to FIG. 1, skirt 16 can be formed, for example, of polyethylene terephthalate (PET) ribbon. The thickness of the skirt can vary, but is desirably less than 6 mil, and desirably less than 4 mil, and even more desirably about 2 mil Skirt 16 can be secured to the inside of frame 12 via Lenzing sutures 56, as shown in FIG. 1. Leaflet structure 14 can be attached to the skirt via a thin PET reinforcing strip 68 (or sleeve), discussed below, which enables a secure suturing and protects the pericardial tissue of the leaflet structure from tears. Leaflet structure 14 can be sandwiched between skirt 16 and the thin PET strip 68 as shown. Suture 58, which secures the PET strip and the leaflet structure 14 to skirt 16 can be any suitable suture, such as an Ethibond suture. Suture 58 desirably tracks the curvature of the bottom edge of leaflet structure 14, as described in more detail below. Leaflet structure 14 can be formed of bovine pericardial tissue, biocompatible synthetic materials, or various other suitable natural or synthetic materials as known in the art and described in U.S. Pat. No. 6,730,118, which is incorporated by reference herein.

Figure 6:
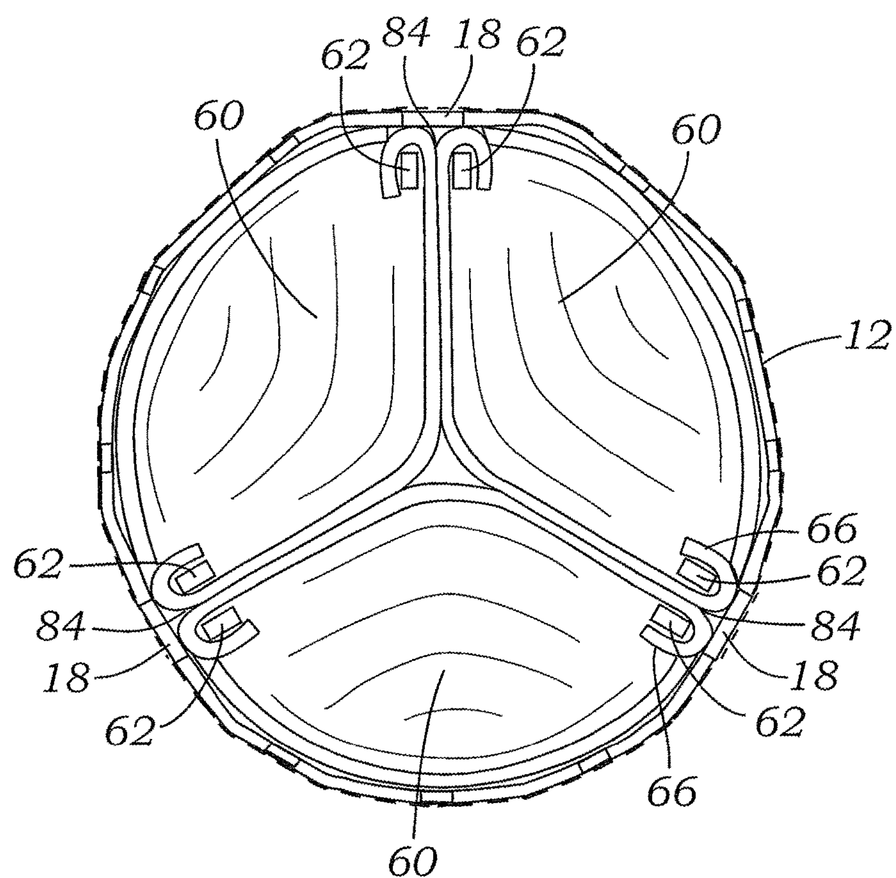
FIG. 6 is a top plan view of the prosthetic valve of FIG. 1.

Leaflet structure 14 can comprise three leaflets 60, which can be arranged to collapse in a tricuspid arrangement, as best shown in FIGS. 2 and 6. The lower edge of leaflet structure 14 desirably has an undulating, curved scalloped shape (suture line 58 shown in FIG. 1 tracks the scalloped shape of the leaflet structure). By forming the leaflets with this scalloped geometry, stresses on the leaflets are reduced, which in turn improves durability of the valve. Moreover, by virtue of the scalloped shape, folds and ripples at the belly of each leaflet (the central region of each leaflet), which can cause early calcification in those areas, can be eliminated or at least minimized. The scalloped geometry also reduces the amount of tissue material used to form leaflet structure, thereby allowing a smaller, more even crimped profile at the inflow end of the valve.

Figure 11:
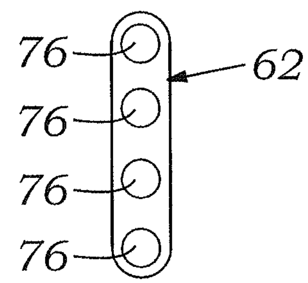
FIG. 11 is a front view of a reinforcing bar that can be used to reinforce the connection of the valve leaflets to a frame in a prosthetic valve such as shown in FIG. 1.

Leaflets 60 can be secured to one another at their adjacent sides to form commissures 84 of the leaflet structure (the edges where the leaflets come together). Leaflet structure 14 can be secured to frame 12 using suitable techniques and mechanisms. For example, as best shown in FIG. 6, commissures 84 of the leaflet structure desirably are aligned with the support posts 18 and secured thereto using sutures. The point of attachment of the leaflets to the posts 18 can be reinforced with bars 62 (FIG. 11), which desirably are made of a relatively rigid material (compared to the leaflets), such as stainless steel.

Figure 12:
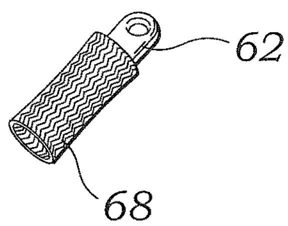
FIG. 12 is a perspective view of the reinforcing bar of FIG. 11 and a PET sleeve that can be used to cover the bar.
Figure 13:
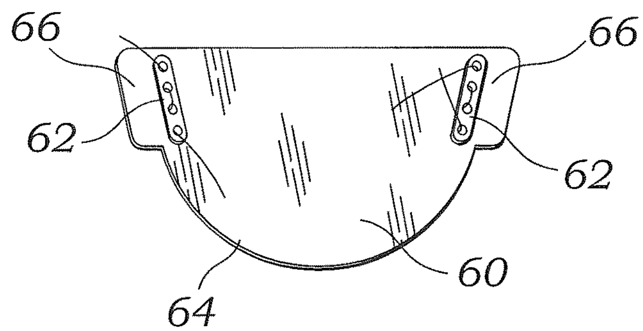
FIG. 13 is a flattened view of a leaflet of the valve shown in FIG. 1.
Figure 18:
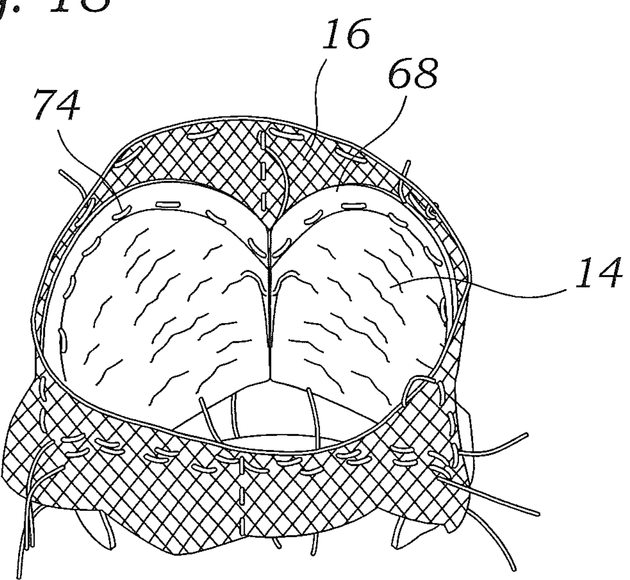
FIG. 18 is a bottom perspective view of the leaflet structure connected to the skirt so as to form a leaflet assembly.

FIG. 13 shows a single leaflet 60, which has a curved lower edge 64 and two flaps 66 extending between the upper edge and curved lower edge of the leaflet. The curved lower edge 64 forms a single scallop. When secured to two other leaflets to form leaflet structure 14, the curved lower edges of the leaflets collectively form the scalloped shaped lower edge portion of the leaflet structure (as best shown in FIG. 18). As further shown in FIG. 13, two reinforcing bars 62 can be secured to the leaflet adjacent to flaps 66 (e.g., using sutures). The flaps can then be folded over bars 62 and secured in the folded position using sutures. If desired, as shown in FIG. 12, each bar 62 can be placed in a protective sleeve 68 (e.g., a PET sleeve) before being secured to a leaflet.

Figure 14:
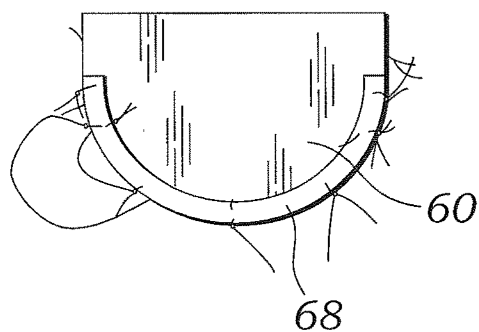
FIG. 14 is a flattened view of the opposite side of the leaflet showing a reinforcing strip secured adjacent the bottom edge of the leaflet.
Figure 15:
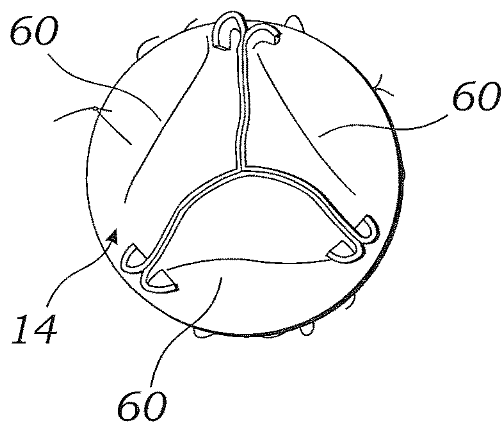
FIG. 15 is a top plan view of the leaflet structure of the valve of FIG. 1 prior to attachment to the frame.

As shown in FIG. 14, the lower curved edge 64 of the leaflet can be reinforced for later securement to the skirt 16, such as by securing a reinforcing strip 68 along the curved lower edge between flaps 66 on the side of the leaflet opposite bars 62. Three such leaflets 60 can be prepared in the same manner and then connected to each other at their flaps 66 in a tricuspid arrangement to form leaflet structure 14, as shown in FIG. 15. The reinforcing strips 68 on the leaflets collectively define a ribbon or sleeve that extends along the lower edge portion of the inside surface of the leaflet structure.

As noted above, leaflet structure 14 can be secured to frame 12 with skirt 16. Skirt 16 desirably comprises a tough, tear resistant material such as PET, although various other synthetic or natural materials can be used. Skirt 16 can be much thinner than traditional skirts. In one embodiment, for example, skirt 16 is a PET skirt having a thickness of about 0.07 mm at its edges and about 0.06 mm at its center. The thinner skirt can provide for better crimping performances while still providing good perivalvular sealing.

Figure 16:
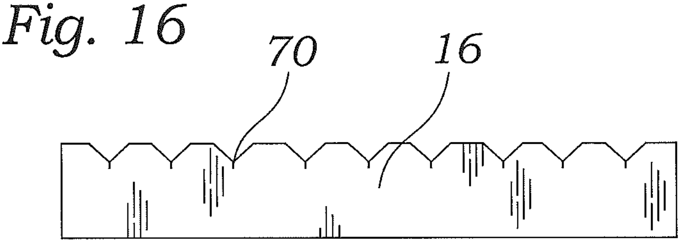
FIG. 16 is a flattened view of the skirt used in the valve shown in FIG. 1.
Figure 17:
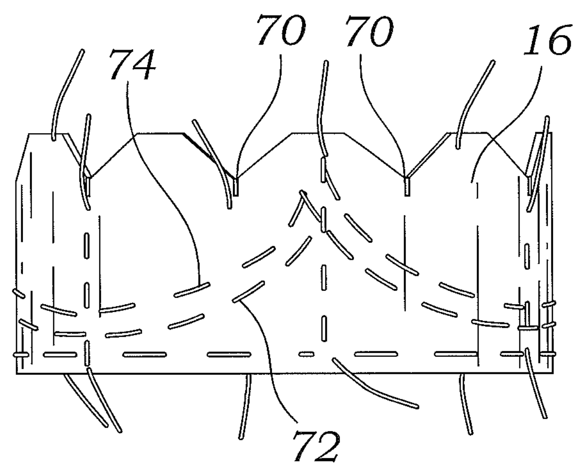
FIG. 17 is a side view of the skirt illustrating suture lines for attaching the skirt to the leaflet structure.

FIG. 16 shows a flattened view of the skirt before the opposite ends are secured to each other to form the annular shape shown in FIG. 17. As shown, the upper edge of skirt 16 desirably has an undulated shape that generally follows the shape of the second row of struts 22 of the frame. In this manner, the upper edge of skirt 16 can be tightly secured to struts 22 with sutures 56 (as best shown in FIG. 1). Skirt 16 can also be formed with slits 70 to facilitate attachment of the skirt to the frame. Slits 70 are aligned with crown structures 26 of struts 22 when the skirt is secured to the frame. Slits 70 are dimensioned so as to allow an upper edge portion of skirt to be partially wrapped around struts 22 and reduce stresses in the skirt during the attachment procedure. For example, in the illustrated embodiment, skirt 16 is placed on the inside of frame 12 and an upper edge portion of the skirt is wrapped around the upper surfaces of struts 22 and secured in place with sutures 56. Wrapping the upper edge portion of the skirt around struts 22 in this manner provides for a stronger and more durable attachment of the skirt to the frame. Although not shown, the lower edge of the skirt can be shaped to conform generally to the contour of the lowermost row of struts 22 to improve the flow of blood past the inflow end of the valve.

As further shown in FIG. 17, various suture lines can be added to the skirt to facilitate attachment of the skirt to the leaflet structure and to the frame. For example, a scalloped shaped suture line 72 can be used as a guide to suture the lower edge of the leaflet structure at the proper location against the inner surface of the skirt using suture 59 (as best shown in FIG. 5). Another scalloped shaped suture line 74 (FIG. 17) can be use as a guide to suture the leaflet structure to the skirt using sutures 58 (FIG. 1). Reinforcing strips 68 secured to the lower edge of the leaflets reinforces the leaflets along suture line 58 and protects against tearing of the leaflets. FIG. 18 shows a leaflet assembly comprised of skirt 16 and leaflet structure 14 secured to the skirt. The leaflet assembly can then be secured to frame 12 in the manner described below. In alternative embodiments, the skirt, without the leaflet structure, can be connected to the frame first, and then the leaflet structure can be connected to the skirt.

FIG. 6 shows a top view of the valve assembly attached to frame 12. Leaflets 60 are shown in a generally closed position. As shown, the commissures of the leaflets are aligned with posts 18 of the frame. The leaflets can be secured to the frame using sutures extending through flaps 66 of the leaflets, openings 76 in bars 62, and openings 78 in posts 18, effectively securing flaps 66 to posts 18. As noted above, bars 62 reinforce the flaps at the area of connection with posts and protect against tearing of the leaflets.

Figure 6A:
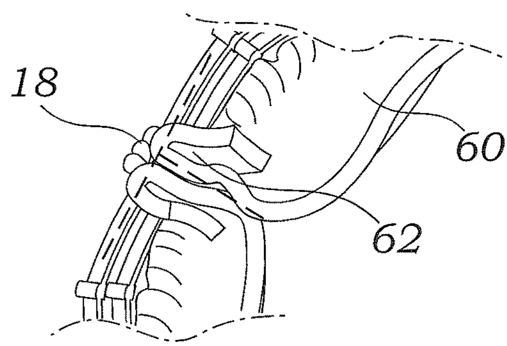
FIG. 6A is an enlarged partial top view of the valve of FIG. 1 illustrating the positioning of the reinforcing bars with respect to the commissure attachment posts of the frame.

As shown in FIG. 6A, bars 62 desirably are aligned perpendicular and as straight as possible with respect to posts 18 of the frame, such that bars 62 and post 18 at each commissure form a "T" shape. The width of bars 62 and the attachment of the commissures via the bars provides a clearance between the deflectable portions of the leaflets 60 (the portions not secured by sutures to the frame) and the frame, while the edge radius (thickness) of bars 62 serves as a flex hinge for the leaflets 60 during valve opening and closing, thereby increasing the space between the leaflets and the frame. By increasing the space between the moving portions of the leaflets and frame and by having the leaflets flex against an edge radius of bars 62, contact between the moving portions of the leaflets (especially the outflow edges of the leaflets) and the frame can be avoided during working cycles, which in turn improves the durability of the valve assembly. This configuration also enhances perfusion through the coronary sinuses.

Figure 19:
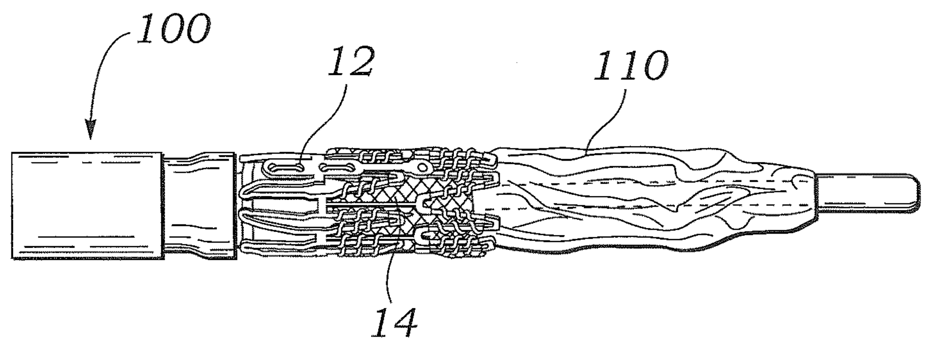
FIG. 19 is a side view of a balloon catheter and a prosthetic valve crimped onto the balloon of the balloon catheter.

FIG. 19 depicts a side view of a valve 10 crimped on a balloon delivery catheter 100. The valve is crimped onto balloon 110 of balloon catheter 100. It is desirable to protect leaflet structure 14 of the valve from damage during crimping to ensure durability of the leaflet structure and at the same time, it is desirable to reduce as much as possible the crimped profile size of the valve. During the crimping procedure the tissue of the leaflet structure (e.g., bovine pericardial tissue or other suitable tissue) is pressed against against the inner surface of the metal frame and portions of the tissue can protrude into the open cells of the frame between the struts and can be pinched due to the scissor-like motion of the struts of the frame. If the valve is severely crimped to achieve a small crimping size, this scissor-like motion can result in cuts and rupture of the tissue leaflets.

Skirt 16, described above, can protect against damage to the leaflet structure during crimping to a certain degree. However, the skirt's main purpose is structural and it does not in certain embodiments cover the entire frame. Therefore, in such embodiments, the skirt may not fully protect the leaflet structure during crimping and as such, the frame can still cause damage to the leaflet structure.

Figure 20:
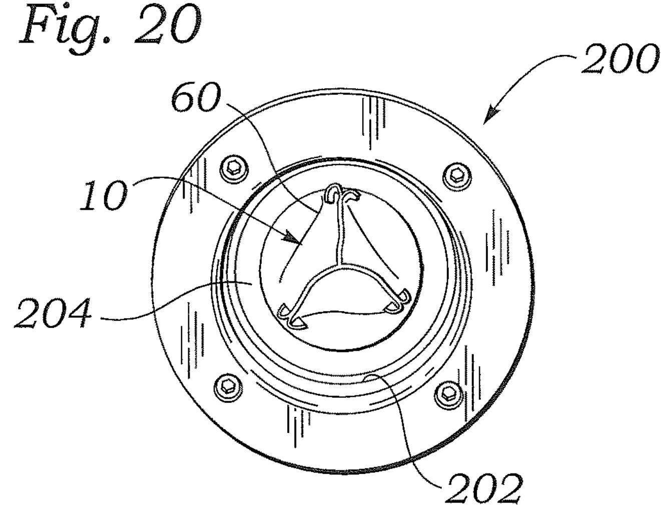
FIG. 20 is a front view of a crimping device showing a prosthetic valve positioned in the crimping aperture of the crimping device with a protective sleeve disposed between the valve and the crimping jaws.
Figure 21:
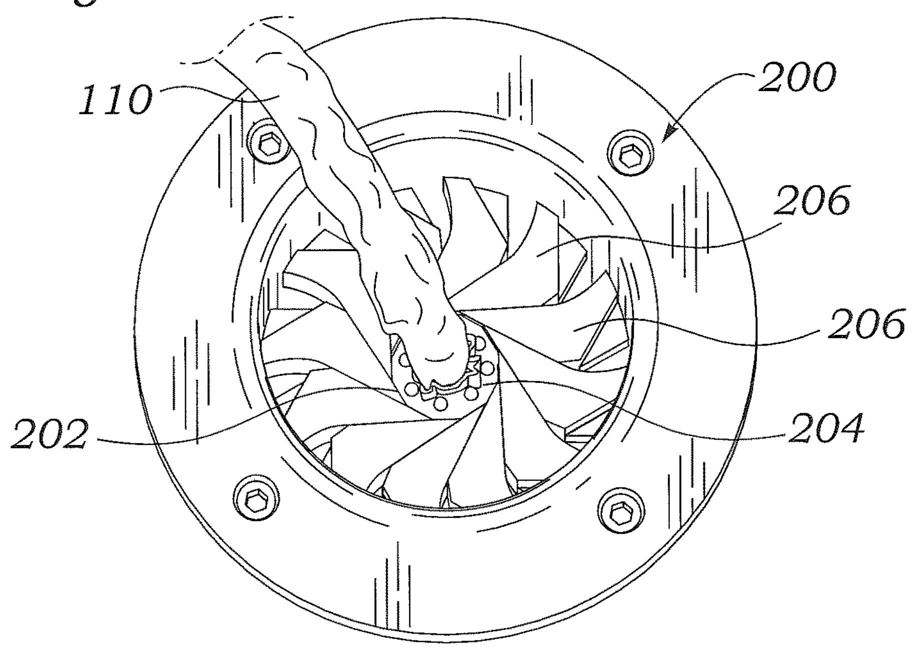
FIG. 21 is a front view of the crimping device shown after the crimping jaws are forced inwardly to compress the valve and the protective sleeve.
Figure 22:
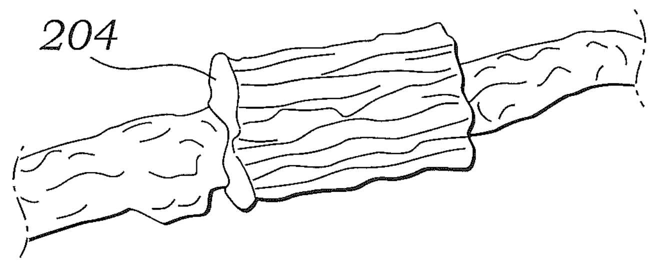
FIG. 22 is a side view of the valve and protective sleeve after removal from the crimping device.

FIGS. 20 and 21 show an embodiment of a crimping apparatus for atraumatic crimping of a valve onto a balloon in a manner that further protects against damage to the leaflets. The crimping apparatus (also referred to as a crimper), indicated generally at 200, has an aperture 202 sized to receive a valve in an expanded state. FIG. 20 shows aperture 202 in a fully open or dilated state with a valve 10 positioned inside aperture 202. Crimping apparatus 200 has a plurality of crimper jaws 206 (12 in the illustrated embodiment) which are configured to move radially inwardly to radially compress (crimp) the valve to a smaller profile around the balloon of a balloon catheter.

A deformable material is positioned between the outside of the frame and the crimping jaws 206. In the illustrated embodiment, the deformable material comprises a protective sleeve, or covering, 204 that is placed around the valve so that it covers the outer surface of the frame of the valve and prevents the hard surface of the crimping jaws from directly contacting the frame of the valve. The sleeve 204 desirably is sized to fully cover the outer surface of the frame. Sleeve 204 desirably is made of a soft, flexible and compressible material. The sleeve can be formed from generally available materials, including, but not limited to, natural or synthetic sponge (e.g., polyurethane sponge), a foamed material made of a suitable polymer such as polyurethane or polyethylene, or any of various suitable elastomeric materials, such as polyurethane, silicon, polyolefins or a variety of hydrogels, to name a few.

The sleeve is desirably stored in a wet environment (e.g., immersed in saline) prior to use. After placing sleeve 204 around the valve, the valve and the sleeve are placed into crimping apparatus 200 as shown in FIG. 20. Balloon 110 of a balloon catheter can then be positioned within the leaflets 60 of the valve (FIG. 21). FIG. 21 shows crimper jaws 206 surrounding sleeve 204, which in turn surrounds frame 12 and leaflet structure 14 of valve 10. Balloon 110 typically is placed at the center of the valve so that the valve can be evenly expanded during implantation of the valve within the body.

As seen in FIG. 21, during crimping, the sponge-like material of protective sleeve 204 protrudes into the open cells of frame 12 and occupies this space, thereby preventing leaflet structure 14 from entering this space and being pinched or otherwise damaged. After crimping is completed, the valve with the protective sleeve is removed from the crimping apparatus. Sleeve 204 can then be gently peeled away from the frame. Because the protective sleeve presses the leaflet structure inwardly and away from the frame during crimping, the valve can be crimped to a small profile without damaging the leaflet structure.

Figure 23:
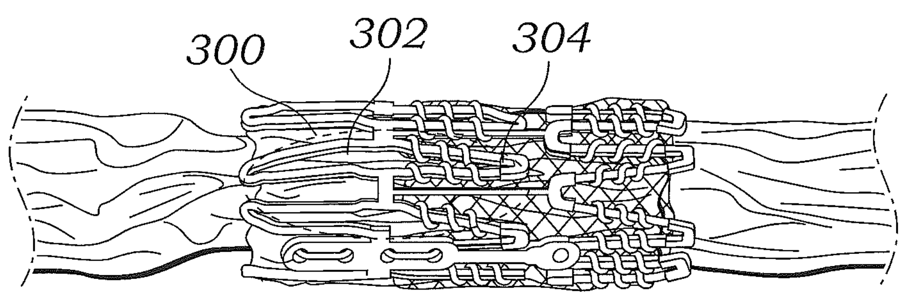
FIG. 23 is a side view of a prosthetic valve that has been crimped onto a balloon of a balloon catheter without a protective sleeve.
Figure 24:
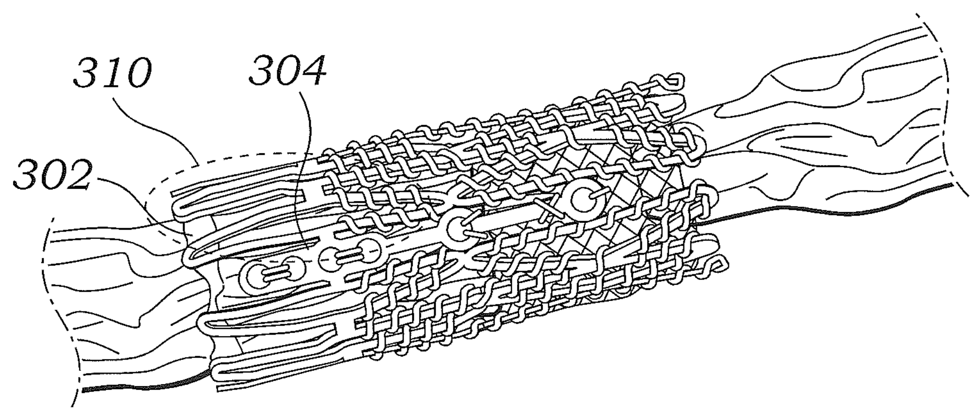
FIG. 24 is a side view of a prosthetic valve that has been crimped onto a balloon of a balloon catheter using a protective sleeve in the manner shown in FIGS. 20-21.

FIGS. 23 and 24 illustrate an advantage that can be gained by using protective sleeve 204. FIG. 23 shows a prosthetic valve that was crimped without using the protective sleeve. Dotted line 300 identifies an area of the valve where leaflet structure 302 has been pressed between struts of a frame 304, which can damage the leaflet structure as discussed above.

In contrast, FIG. 24 shows a prosthetic valve that was crimped using protective sleeve 204. In this example, leaflet structure 302 was pressed inwardly and away from the inside of frame 304 and, therefore, the leaflet structure was not pinched or squeezed between the struts of the frame.

Accordingly, since the leaflet structure is pushed away from the frame when the protective sleeve is used, the leaflet structure is less likely to be pinched or cut during the crimping process. Also, when using a protective sleeve, a very ordered structure of balloon-leaflets-frame (from inward to outward) can be achieved. When no such protective sleeve is utilized, some portion of the balloon, leaflets, and frame are much more likely to overlap after the crimping procedure and the resulting structure is less predictable and uniform.

In addition to the foam or sponge-type protective sleeve described above, other types of sleeves or protective layers of deformable material can be used to protect the leaflets against damage during crimping of a valve. In one implementation, for example, a layer (e.g., rectangular slices) of deformable material (e.g., sponge, rubber, silicon, polyurethane, etc.) can be disposed on each crimping jaw 206 so as to form a sleeve around the valve upon crimping. Alternatively, deformable packets filled with a flowable, deformable material, such as a gel or gas, can be disposed on each crimping jaw for contacting the valve upon crimping. In addition, the deformable material (e.g., sleeve 204) can be covered with a thin PET cloth, among many other fabric materials or other suitable materials, to prevent particles of the deformable materials from migrating to the valve during crimping.

The skirt of a prosthetic valve serves several functions. In particular embodiments, for example, the skirt functions to seal and prevent (or decrease) perivalvular leakage, to anchor the leaflet structure to the frame, and to protect the leaflets against damage caused by contact with the frame during crimping and during working cycles of the valve. The skirt used with the prosthetic valve discussed above has been described as being a fabric, such as a PET cloth. PET or other fabrics are substantially non-elastic (i.e., substantially non-stretchable and non-compressible). As such, the skirt in certain implementations limits the smallest achievable crimping diameter of the valve and can wrinkle after expansion from the crimped diameter.

In alternative embodiments, such as discussed below, a prosthetic valve can be provided with a skirt that is made of a stretchable and/or compressible material, such as silicon. Due to the compressibility of such a skirt, the valve can be crimped to a relatively smaller diameter as compared to a valve having a non-compressible skirt. Furthermore, such a skirt can recover its original, smooth surfaces with little or no wrinkling after expansion from the crimped state.

Figure 25:
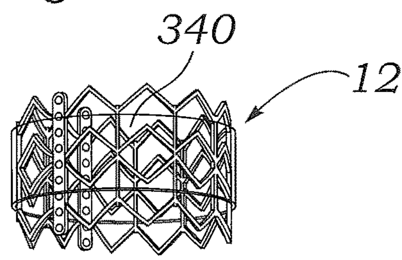
FIG. 25 is a side view of a frame for a prosthetic valve having a silicon skirt, or sleeve, disposed on the outside of the frame.

FIG. 25 shows an embodiment of a frame 12 that has an elastic "over-tube" skirt or sleeve 340 that extends completely around and covers at least a portion of the outside of the frame. In particular embodiments, skirt 340 is made of silicon, which can undergo large deformations while maintaining its elasticity. Such a silicon skirt can be a thin sleeve that covers a portion of frame 12 from the outside. In the illustrated embodiment, the height of the skirt is less than the overall height of frame 12, however, the skirt can vary in height and need not be the height shown in FIG. 25. For example, the height of the skirt can be the same as or greater than that of the frame so as to completely cover the outside of the frame. In an alternative embodiment, the skirt 340 can be mounted to the inside of the frame using, for example, sutures or an adhesive. When mounted inside of the frame, the skirt can protect the leaflets from abrasion against the inside of the frame. Other materials that can be used to form the skirt or sleeve include, but are not limited to, PTFE, ePTFE, polyurethane, polyolefins, hydrogels, biological materials (e.g., pericardium or biological polymers such as collagen, gelatin, or hyaluronic acid derivatives) or combinations thereof.

Figure 26:
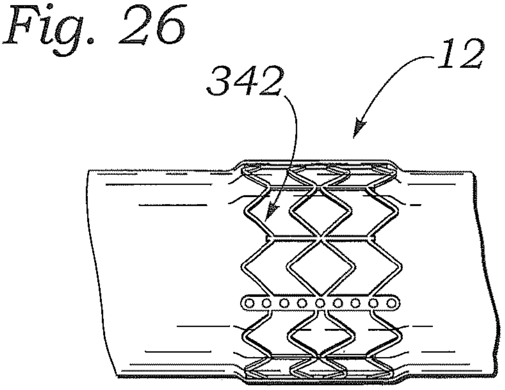
FIG. 26 is a side view of a frame for a prosthetic valve having a silicon encapsulating layer covering the inside and outside of the frame.

In another embodiment, the entire frame or a portion thereof can be dipped in liquefied material (e.g., liquid silicon or any of the materials described above for forming the sleeve 340 that can be liquefied for dip coating the frame) in order to encapsulate the entire frame (or at least that portion that is dipped) in silicon. FIG. 26 is a side view of a frame 12 that has been dipped in silicon to form a continuous cylindrical silicon covering 342 encapsulating the struts of the frame and filling the spaces between the struts. FIG. 26 shows the covering 342 before it is trimmed to remove excess material extending beyond the ends of the frame. Although less desirable, the frame can be dipped such that the silicon encapsulates the struts of the frame but does not fill the open spaces between the struts of the frame.

Figure 27:
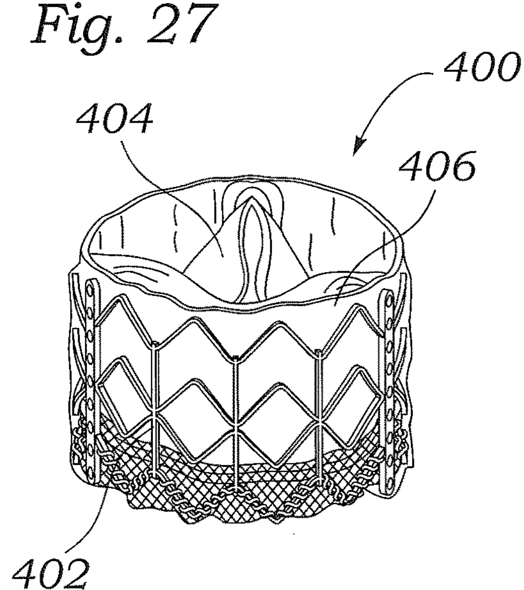
FIG. 27 is a perspective view of a prosthetic valve comprising a frame having a silicon encapsulating layer.
Figure 28:
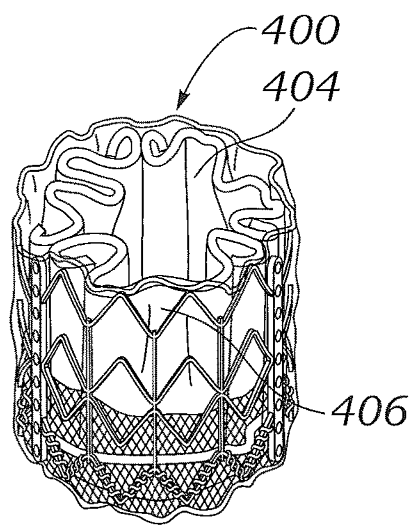
FIG. 28 is a perspective view of the valve of FIG. 27 after it has been crimped to a smaller diameter.
Figure 29:
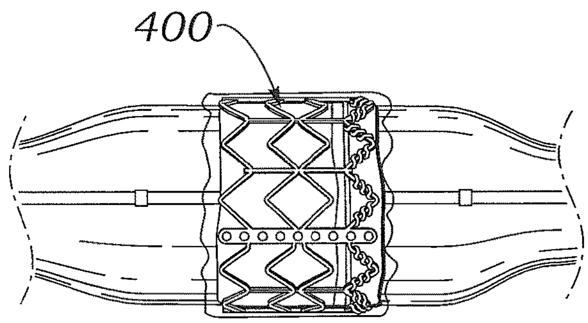
FIG. 29 is a side view of the valve of FIG. 27 after it has been expanded by a balloon catheter.

FIG. 27 shows an embodiment of a prosthetic valve 400 comprising a frame 402 and a leaflet structure 404 mounted to the inside of the frame (e.g., using sutures as shown). Frame 402 has a skirt in the form of silicon covering 406 that is formed, for example, by dipping the frame into liquid silicon. FIG. 27 shows valve 400 in its expanded state. In FIG. 28, valve 400 has been crimped to a smaller profile. During crimping, coating 406, which extends across and fills the open cells between the struts of the frame, is effective to push leaflet structure 404 inward and away from the frame, thereby protecting the leaflet structure from pinching or tearing. FIG. 29 shows valve 400 after being expanded by a balloon of a balloon catheter.

Figure 30A:
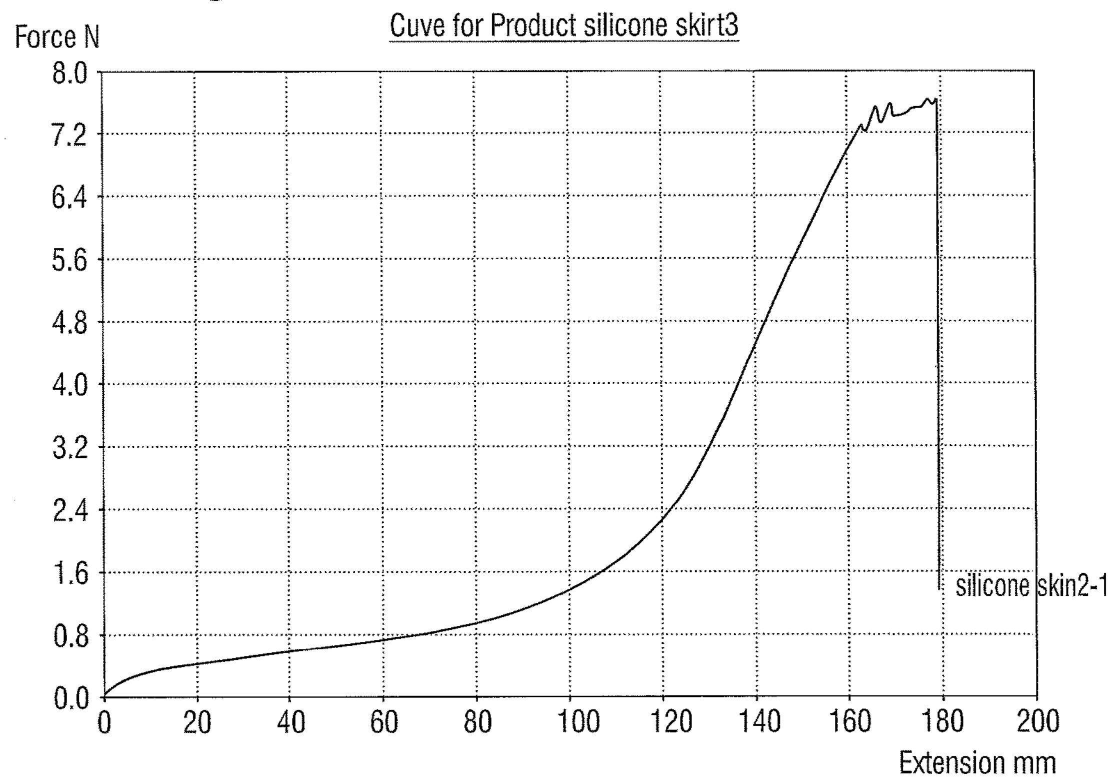
FIGS. 30A-30C are graphs illustrating the results of respective uniaxial tests performed on respective silicon test strips.
Figure 30B:
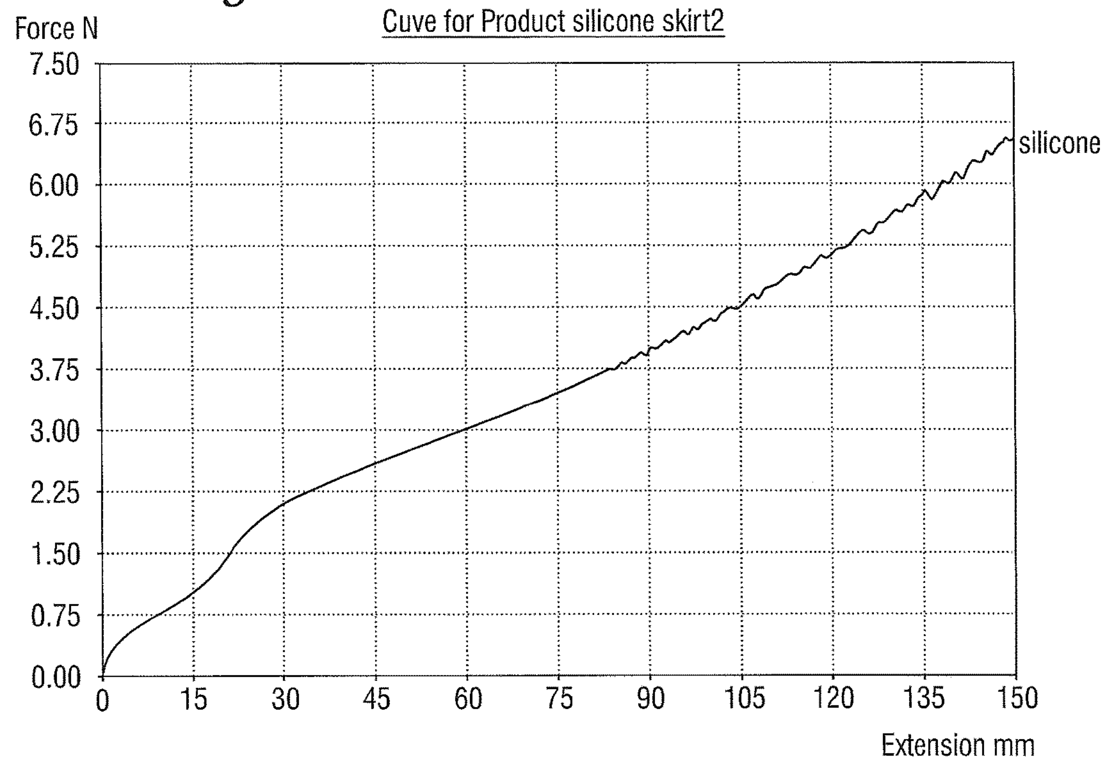
Figure 30C:
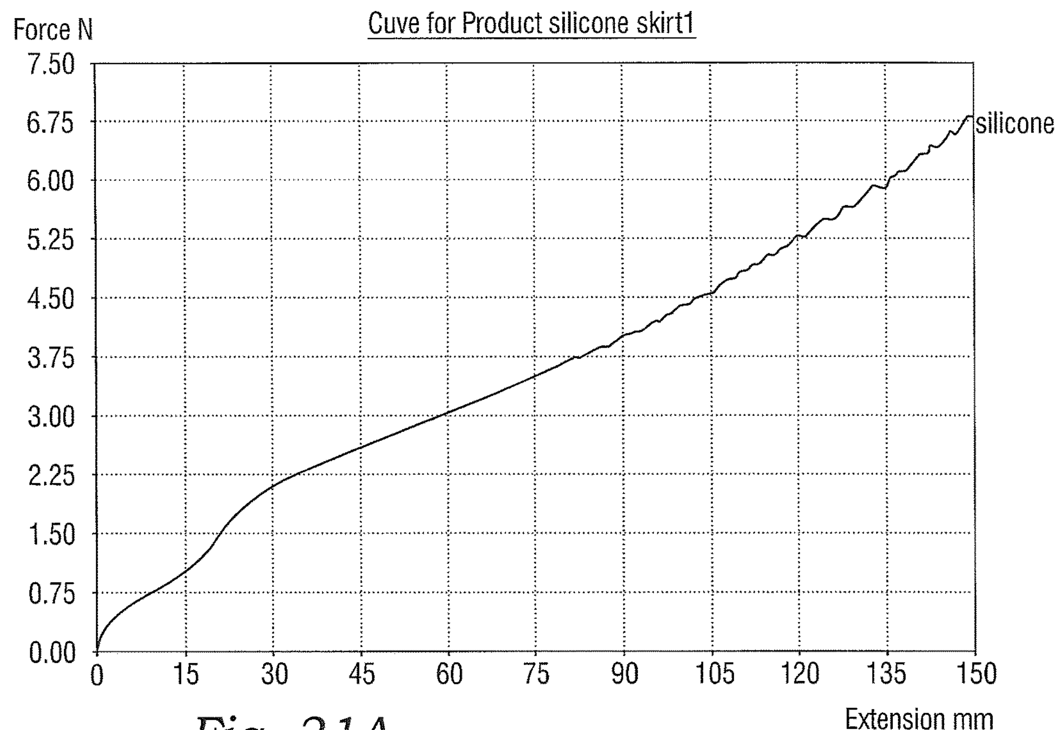
Figure 31A:
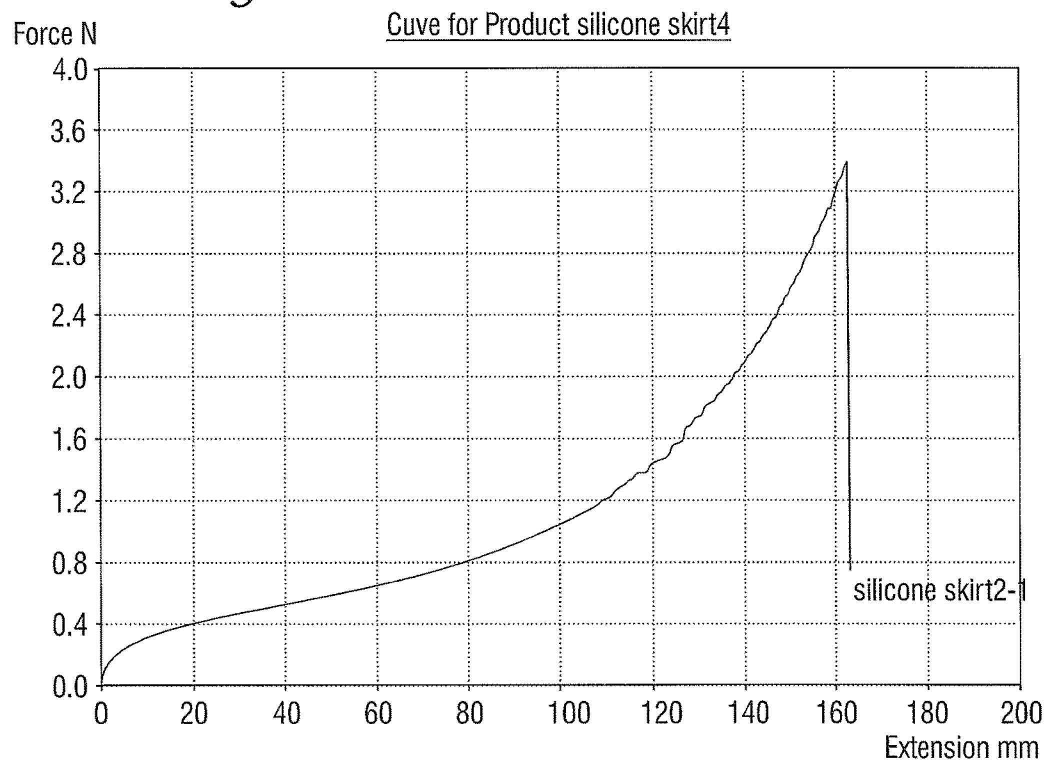
FIGS. 31A-31F are graphs illustrating the results of respective uniaxial tests performed on respective silicon test strips having deliberately introduced tears.
Figure 31B:
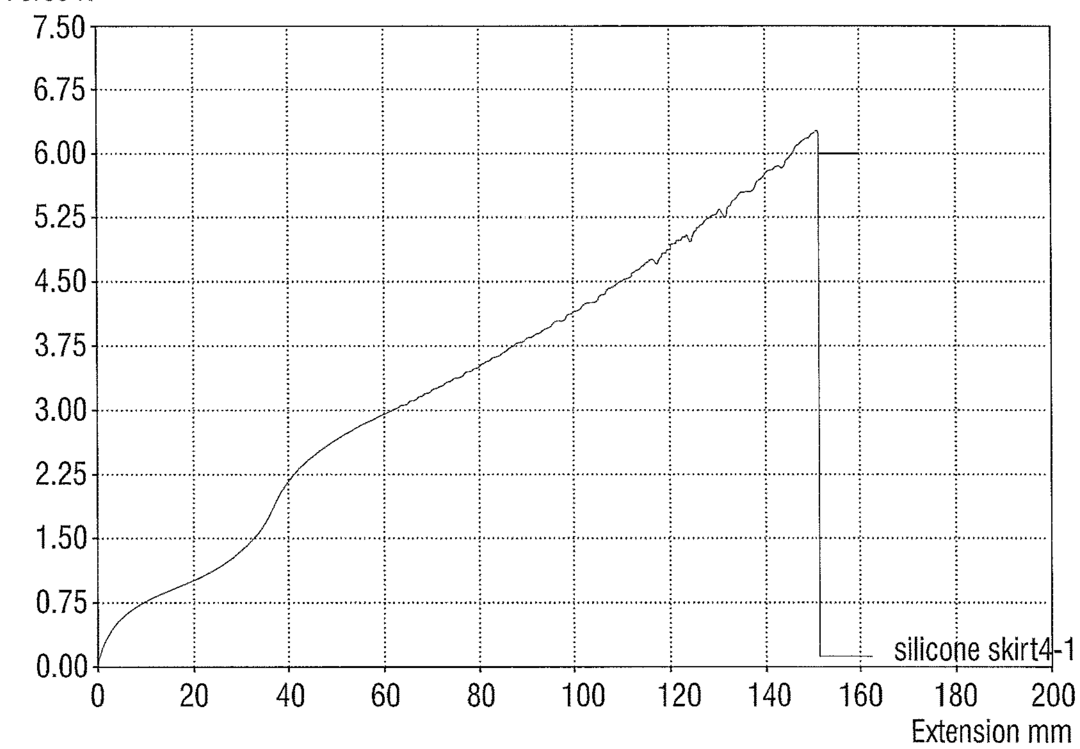
Figure 31C:
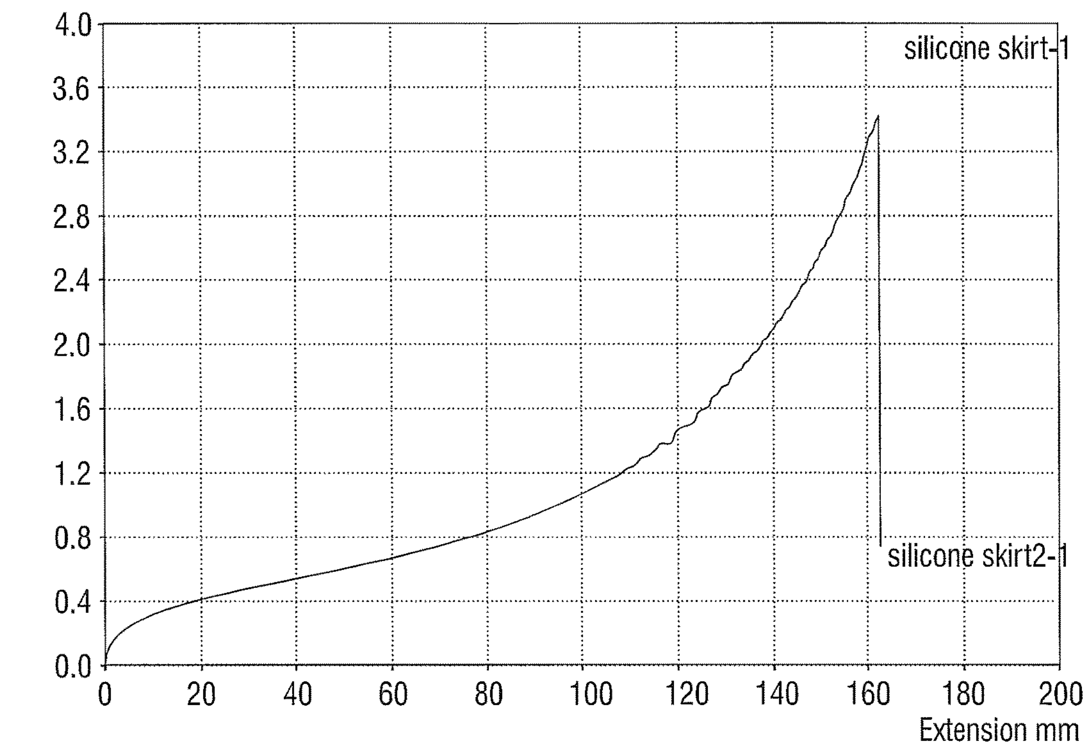
Figure 31D:
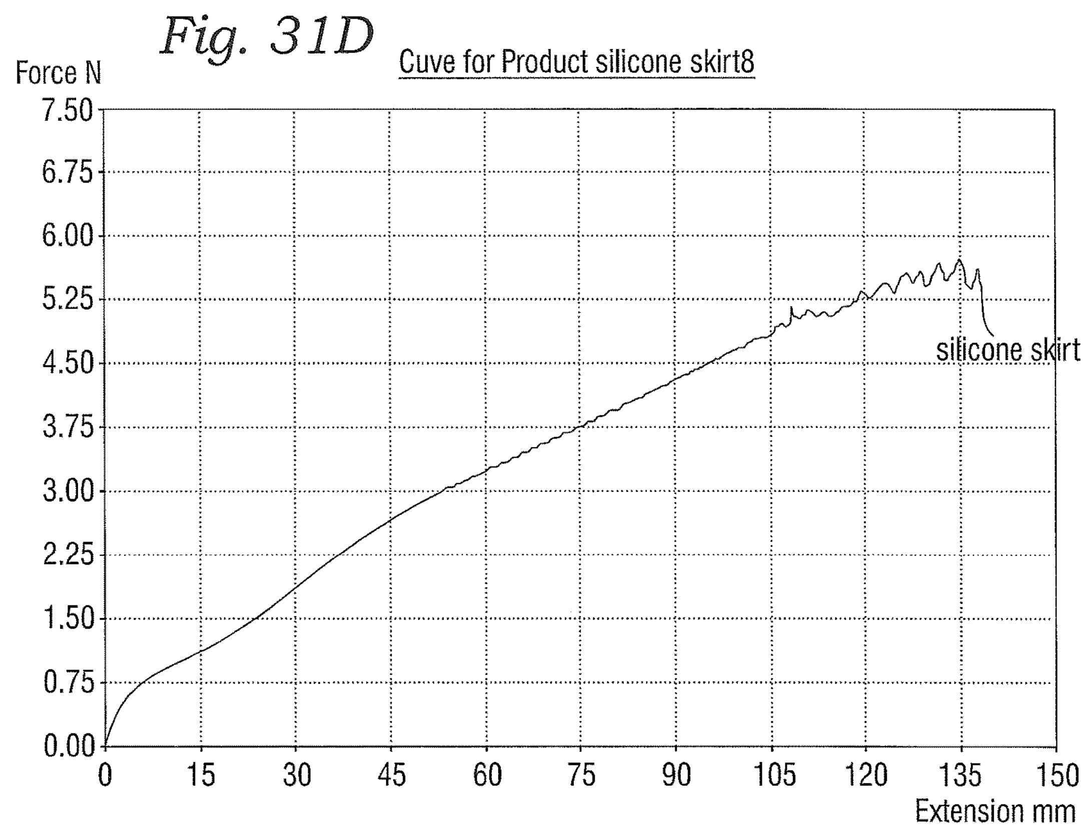
Figure 31E:
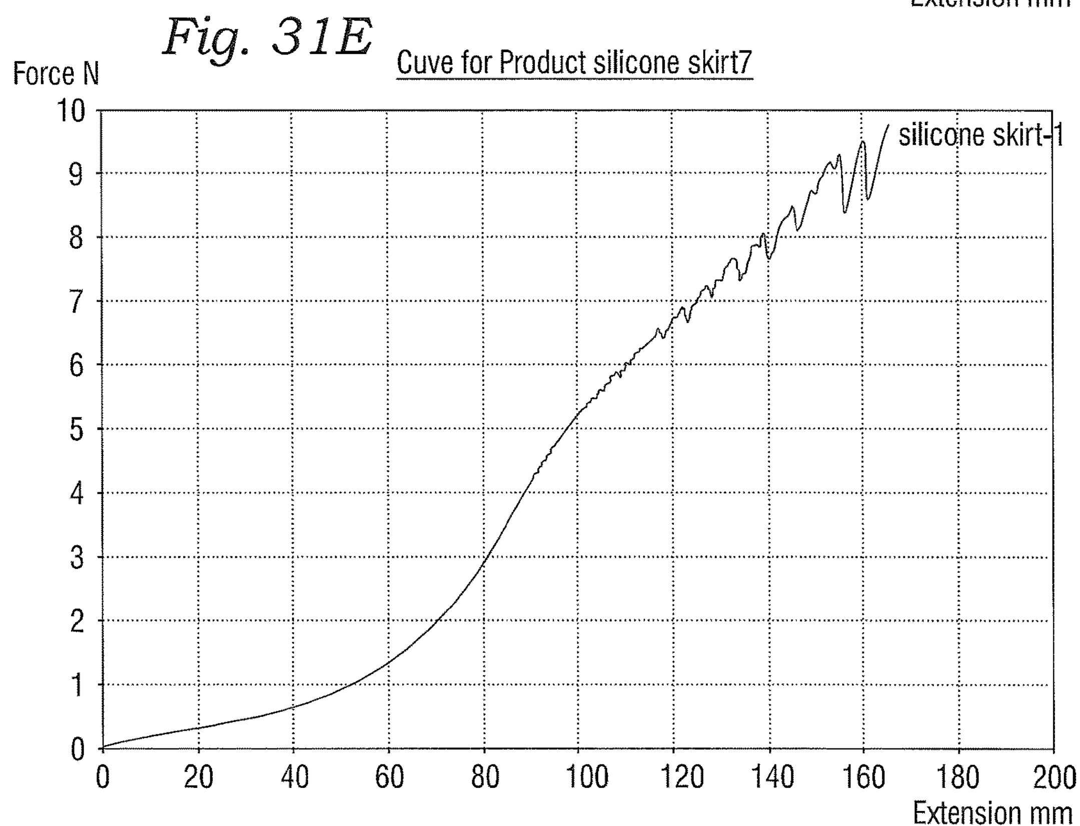
Figure 31F:
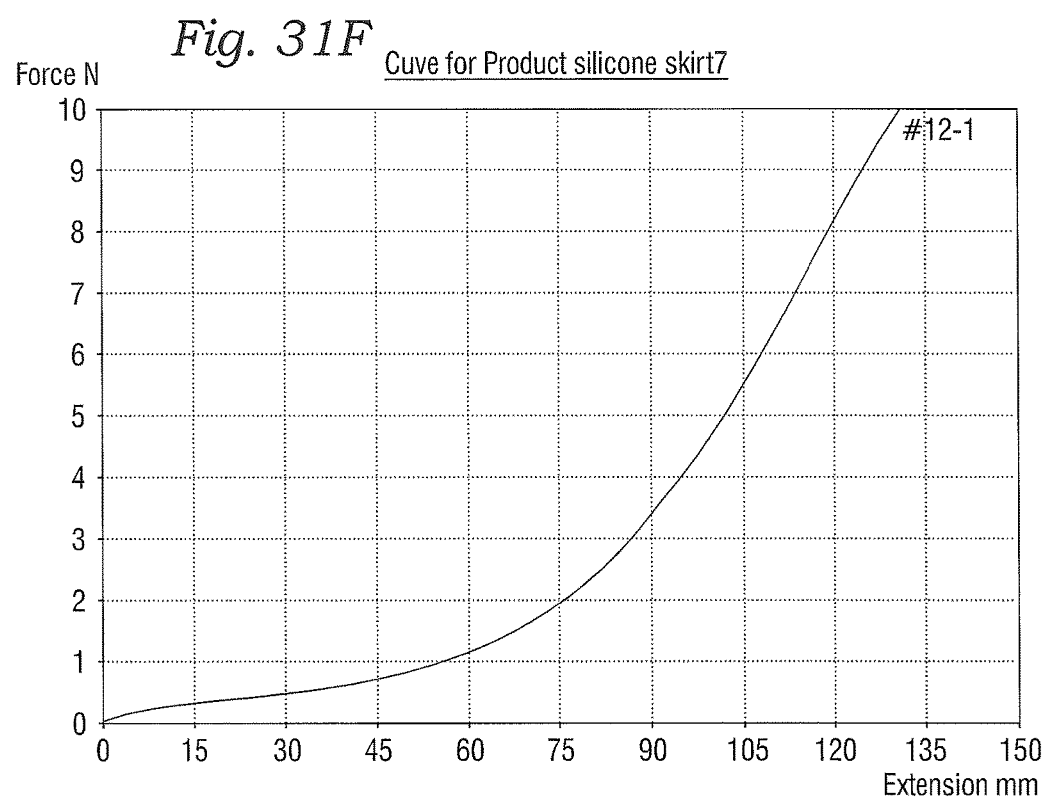

In order to test the durability and stretch resistance of the silicon used, several uniaxial tests were conducted. In particular, silicon strips of about 5×50 mm (with a thickness of about 0.85 mm) were tested in a uniaxial tester. FIGS. 30A-30C show graphs of the results of the uniaxial testing of silicon strips. In addition, tears were deliberately introduced into silicon strips at a middle of the strips and at the edge of the strips while the strips were stretched on a uniaxial tester. The tears were introduced by making holes in the silicon strips with a needle. FIGS. 31A-31F show graphs of the results of the uniaxial testing of silicon strips with deliberately introduced tears.

It was found that ultimate tensile stretch for a thin layer of silicon was over 500% and that samples that had tears that were deliberately introduced continued to show notable strength. Accordingly, the elasticity of silicon permits silicon dipped frames to be crimped to very low profiles and expanded back out to larger profiles without significant damage to the silicon layer. In addition, the silicon material can increase friction between the frame and the native annulus where the prosthetic valve is implanted, resulting in better anchoring and preventing/reducing perivalvular leaks.

A silicon skirt can be mounted on a frame by various means, including by using a mandrel. Also, it may be desirable to use a silicon skirt in combination with a cloth or fabric skirt. For example, it may be desirable to place a silicon skirt on the outside of a cloth or fabric skirt that is surrounding at least a portion of a frame.

Alternatively or additionally, a silicon skirt could also be placed on the inside of the frame and attached to the frame so that it offers the leaflets improved protecting during working cycles. Alternatively, instead of silicon, the skirt can be made of an auxetic and/or swelling material, such as synthetic or natural hydrogels. An auxetic material is one that expands laterally while stretched longitudinally, which means that this material has a negative Poisson ration. If the frame is covered with an auxetic material it can expand radially while being stretched circumferentially when the valve is expanded from its crimped state. Such expansion can improve the fit of the valve at the native valve annulus, thereby preventing or reducing perivalvular leakage.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A system comprising:

an implantable prosthetic valve having a radially collapsible and expandable annular frame and tissue leaflets mounted inside of the frame;

a crimping apparatus having a plurality of crimping jaws arranged to form an aperture sized to receive the implantable prosthetic valve and to radially collapse the implantable prosthetic valve from a first, expanded state to a second, radially collapsed state; and a layer of deformable material configured to be positioned as an intermediate protective layer between the plurality of crimping jaws of the crimping apparatus and the frame of the implantable prosthetic valve, wherein the layer of deformable material comprises an annular sleeve configured to be placed around the implantable prosthetic valve, and wherein the layer of deformable material can be removed from the implantable prosthetic valve prior to implanting the implantable prosthetic valve.

2. The system of claim 1, further comprising a balloon catheter, wherein the implantable prosthetic valve is configured to be crimped onto the balloon catheter in the radially collapsed state by the crimping apparatus.

3. The system of claim 1, wherein the layer of deformable material is configured to fully cover the frame of the implantable prosthetic valve.

4. The system of claim 1, wherein the annular sleeve comprises a sponge material.

5. The system of claim 1, wherein the annular sleeve comprises a foamed polymeric material.

6. The system of claim 1, wherein the layer of deformable material comprises at least one deformable packet filled with a flowable and deformable material.

7. The system of claim 1, further comprising a fabric configured to be positioned between the frame of the implantable prosthetic valve and the layer of deformable material.

8. The system of claim 1, wherein the frame comprises a plurality of struts defining multiple openings in the frame, the layer of deformable material being configured to protrude into the openings in the frame as a result of the plurality of crimping jaws pressing the layer of deformable material against the frame.

9. The system of claim 1, wherein the layer of deformable material prevents the crimping jaws from directly contacting the frame.

10. The system of claim 1, wherein the layer of deformable material comprises an elastomer, a sponge, or a foamed material.

11. A system comprising:

an implantable prosthetic valve having a radially collapsible and expandable annular frame and tissue leaflets mounted inside of the frame;

a crimping apparatus having a plurality of crimping jaws arranged to form an aperture sized to receive the implantable prosthetic valve and to radially collapse the implantable prosthetic valve from a first, expanded state to a second, radially collapsed state; and a layer of deformable material configured to be positioned as an intermediate protective layer between the plurality of crimping jaws of the crimping apparatus and the frame of the implantable prosthetic valve, wherein the layer of deformable material comprises an annular sleeve configured to be placed around the implantable prosthetic valve in its expanded state.

12. The system of claim 11, wherein the annular sleeve comprises a sponge material.

13. The system of claim 11, wherein the annular sleeve comprises a foamed polymeric material.

14. The system of claim 11, wherein the annular sleeve comprises a fabric material.

15. The system of claim 14, wherein the fabric material of the annular sleeve comprises polyethylene terephthalate.

16. The system of claim 15, wherein the implantable prosthetic valve further comprises a skirt coupled to the frame, and the skirt comprises polyethylene terephthalate fabric material.

17. The system of claim 11, wherein portions of the annular sleeve extend radially inwardly beyond an inner diameter of the frame and press the leaflets of the implantable prosthetic valve radially inwardly when the implantable prosthetic valve is collapsed to its collapsed state by the crimping jaws.

18. A system comprising:

an implantable prosthetic valve having a radially collapsible and expandable annular frame and tissue leaflets mounted inside of the frame;

a crimping apparatus having a plurality of crimping jaws arranged to form an aperture sized to receive the implantable prosthetic valve and to radially collapse the implantable prosthetic valve from a first, expanded state to a second, radially collapsed state; and a layer of deformable material configured to be positioned as an intermediate protective layer between the plurality of crimping jaws of the crimping apparatus and the frame of the implantable prosthetic valve, wherein the layer of deformable material comprises a plurality of slices of the deformable material mounted on inner surfaces of the jaws, and wherein the layer of deformable material can be removed from the implantable prosthetic valve prior to implanting the implantable prosthetic valve.

19. The system of claim 1, wherein the annular sleeve comprises a polyethylene terephthalate fabric material.

20. The system of claim 1, wherein portions of the annular sleeve extend radially inwardly through open cells of the frame and prevent the leaflets of the implantable prosthetic valve from entering the open cells when the implantable prosthetic valve is collapsed to its collapsed state by the crimping jaws.

21. The system of claim 20, wherein the portions of the annular sleeve that extend through the open cells of the frame press the leaflets radially inwardly relative to the frame when the implantable prosthetic valve is collapsed by the crimping jaws.

22. The system of claim 1, wherein the annular sleeve is configured to be placed around the implantable prosthetic valve when the implantable prosthetic valve is in the expanded state.

* * * * *